(12) United States Patent
Perumal et al.

(10) Patent No.: US 8,669,225 B2
(45) Date of Patent: Mar. 11, 2014

(54) METHOD OF FORMING NON-IMMUNOGENIC HYDROPHOBIC PROTEIN NANOPARTICLES AND USES THEREFOR

(75) Inventors: Omathanu P. Perumal, Brookings, SD (US); Satheesh K. Podaralla, Brookings, SD (US); Radhey S. Kaushik, Brookings, SD (US)

(73) Assignee: South Dakota State University, Brookings, SD (US)

( * ) Notice: Subject to any disclaimer, the term of this patent is extended or adjusted under 35 U.S.C. 154(b) by 451 days.

(21) Appl. No.: 12/991,872

(22) PCT Filed: May 11, 2009

(86) PCT No.: PCT/US2009/002935
§ 371 (c)(1),
(2), (4) Date: Dec. 13, 2010

(87) PCT Pub. No.: WO2009/137112
PCT Pub. Date: Nov. 12, 2009

(65) Prior Publication Data
US 2011/0091565 A1     Apr. 21, 2011

Related U.S. Application Data

(60) Provisional application No. 61/127,134, filed on May 9, 2008.

(51) Int. Cl.
*C07K 14/00* (2006.01)
(52) U.S. Cl.
USPC .............................. 514/2; 530/300; 977/798
(58) Field of Classification Search
None
See application file for complete search history.

(56) References Cited

U.S. PATENT DOCUMENTS

| | | | |
|---|---|---|---|
| 5,254,673 A | 10/1993 | Cook et al. | |
| 5,330,778 A | 7/1994 | Stark et al. | |
| 5,679,377 A | 10/1997 | Bernstein et al. | |
| 2007/0148251 A1* | 6/2007 | Hossainy et al. | ............. 424/489 |
| 2011/0064794 A1* | 3/2011 | Deng et al. | .................... 424/450 |

OTHER PUBLICATIONS

Sonaje et al., "Development of biodegradable nanoparticles for oral delivery of ellagic acid and evaluation of their antioxidant efficacy against cyclosporine A-induced nephrotoxicity in rats", Pharmaceutical Research 24(5) 2007; Epub Mar. 2007.*
Liu et al. Microspheres of corn protein, zein, for an ivermectin drug delivery system. Biomaterials 26 (2005) 109-115.
Lopez et al. Zein microspheres as drug/antigen carriers: A study of their degradation and erosion, in the presence and absence of enzymes. J. Microencapsulation 23 (2006) 303-314.
Parris et al. Encapsulation of Essential Oils in Zein Nanospherical Particles. J.Agric. Food. Chemistry 53 (2005) 4788-4792.
Veronese et al. 'PEGylation, successful approach to drug delivery', Drug Discovery Today, vol. 10, No. 21, Nov. 2005. 1451-1458.
Cevc, Gregor. 'Lipid vesicles and other colloids as drug carriers on the skin', Advanced Drug Delivery Reviews, Mar. 2004, vol. 56. No. 5, pp. 675-711.
Cui F. et al. 'Biodegradable nanoparticles loaded with insulin?phospholipid complex for oral delivery: Preparation, in vitro characterization and in vivo evaluation', Journal of Controlled Release, Aug. 2006, vol. 114, No. 2, pp. 242-250.
Leach WT. et al. 'Encapsulation of protein nanoparticles into uniform-sized microspheres formed in a Spinning Oil Film'. AAAPS PharmSciTech, 2005. vol. 6, No. 4, Article 75, pp. E605-E617.
Li S. et al. 'Pharmacokinetic characteristics and anticancer effects of 5-Fluorouracil loaded nanoparticles', BMC Cancer, Apr. 14, 2008, vol. 8, No. 103, pp. 1-9.(doi: 10.1186/1471-2407-8-103.).
Mason et al. 'Preparation of White Zein From Yellow Corn', Journal of Biological Chemistry, (1934).

* cited by examiner

*Primary Examiner* — Anand Desai
(74) *Attorney, Agent, or Firm* — MDIP LLC

(57) ABSTRACT

Methods are described for producing non-immunogenic nanoparticles from protein sources by controlling the pH in a nanoprecipitation process. The nanoparticles that are produced by the disclosed methods range in diameter size from about 100 ran to about 400 nm, with a preferred diameter size of from approximately 100 nm to approximately 300 nm, thereby rendering them non-immunogenic. The invention further discloses methods for producing nanoconjugates that are suitable for a variety of therapeutic, diagnostic and other uses.

5 Claims, 18 Drawing Sheets

METHOD OF FORMING NON-IMMUNOGENIC HYDROPHOBIC PROTEIN NANOPARTICLES AND USES THEREFOR

CROSS-REFERENCE TO RELATED APPLICATIONS

The present application is a national stage filing of PCT/US2009/002935, filed May 11, 2009, which claims the benefit of priority to U.S. Patent Application No. 61/127,134, filed May 9, 2008, which applications are incorporated by reference herein in their entirety.

TECHNICAL FIELD

This invention relates to methods of forming nanoparticles, and specifically relates to methods of forming nanoparticles from hydrophobic, water-insoluble protein-based polymers to produce non-immunogenic delivery systems for use in pharmaceutical, therapeutic and diagnostic applications.

BACKGROUND

The references discussed herein are provided solely for the purpose of describing the field relating to the invention. Nothing herein is to be construed as an admission that the inventors are not entitled to antedate a disclosure by virtue of prior invention.

Zein is a plant protein isolated from corn or maize and belongs to a family of prolamines which are composed of high amounts of hydrophobic amino acids, such as proline, glutamine and asparagine. Zein is clear, odorless, non-toxic, biodegradable and water-insoluble. Zein has been investigated and used as a polymer in the pharmaceutical, medical, food, cosmetic, adhesive and packaging industries.

In the food and pharmaceutical industries, zein has been used, for example, to film-coat materials and to form particulate systems such as microparticles or nanoparticles [1-5]. Various methods of forming zein particles have been proposed. For example, U.S. Pat. No. 5,330,778, the contents of which are incorporated herein, discusses a method for preparing microparticles using zein, and uses pH alteration to form the zein microparticles [6]. However, the method described in U.S. Pat. No. 5,330,778 produces zein particles with larger micron sizes and with a wide particle size distribution, which has significant drawbacks, for example, for in vivo use.

It is important to ensure that a biomaterial used for human or animal applications is safe and non-immunogenic. In general, upon in vivo administration (e.g., introduction into the body) of particles, phagocytic cells in the blood and tissues, which are responsible for immunological recognition and removal of foreign particles, can initiate an immune response depending on the physicochemical characteristics of the particles. The uptake by phagocytic cells is dependent on both particle size and surface hydrophobicity of the foreign particle. In general, particles in a diameter size range greater than approximately 500 nm are prone to phagocytosis. Particles with a hydrophobic surface are easily recognized by the phagocytic cells [7]. For example, Lopez and Murdan [8] have recently reported that zein microspheres of a diameter of 1.36±0.036 μm are immunogenic and, consequently, are not suitable as a drug, vaccine or other therapeutic carrier.

SUMMARY OF THE INVENTION

In one aspect of the disclosure, the present invention generally relates to a method for producing very small particles, or nanoparticles. The particles may be formed from hydrophobic water-insoluble proteins including, for example, zein.

In another aspect of the disclosure, methods are employed to produce nanoparticles that reduce or substantially overcome the immunogenicity that is experienced in the use of larger-sized nanoparticles or microparticles, including those formed from, for example, hydrophobic water-insoluble proteins. The non-immunogenic effect of the nanoparticles made in accordance with the methods of the present invention is achieved by controlling the size of the particles formed by the method, as well as the range of particle sizes.

In some implementations of the invention, the range of particle diameter sizes is less than approximately 400 nm. In preferred implementations of the invention, the range of particle diameter sizes is less than approximately 300 nm, and in some further implementations the range of particle diameter sizes is approximately 100 nm to approximately 300 nm. While size is discussed in this disclosure in terms of a diameter, this should not be interpreted to imply that the nanoparticles discussed herein are perfectly spherical in shape, although spherical shapes in the nanoparticles may be achieved. It should be understood that the dimensions disclosed herein may simply be measured between opposite sides of the particle, or the largest dimension across the particle from opposite sides.

In one aspect of the invention, the methods of the invention may be carried out using water-insoluble hydrophobic proteins that may be derived from a variety of sources including plant, animal and synthetic sources. In various aspects, the method may be carried out with a family of prolamines which are composed of high amounts of hydrophobic amino acids such as, for example, proline, glutamine and asparagine. These hydrophobic amino acids make the protein water-insoluble. The prolamines may be found in various grains such as corn, wheat, barley, rice, sorghum, and in other plants and animal sources. Some examples of suitable prolamines are zein, gliadin, hordein and kafirin, although the application of the method is not necessarily limited to these examples. For the purposes of this description, and merely as one exemplar illustration of the invention, the methods are described herein using zein, by way of example only.

In various implementations of the method, white zein is utilized to produce nanoparticles in a desirable diameter size range of approximately 100 to approximately 400 nm. It has been found that the use of yellow zein may produce particles with relatively larger diameter size, and may also produce particles with wider particle diameter size distribution. It is believed that the pigments in yellow zein may affect the solubility of the yellow zein and the nanoparticle formation using yellow zein.

The methods of the invention produce nanoparticles of a generally smaller diameter size and narrower diameter size range than would otherwise be possible. These smaller nanoparticles are achieved by implementing a pH-controlled nanoprecipitation process using one or more particular grades of a base protein, such as zein, and by using various combinations of buffers, surfactants, and phospholipids that are selected to achieve nanoparticle sizes and diameters that render the nanoparticles non-immunogenic.

The methods of the disclosure are further suitable for preparing nanoparticles with a wide variety of molecules, particles or agents, having varying physicochemical properties, to form encapsulated, absorbed, complexed or conjugated materials with the nanoparticles. For example, the method may be utilized to entrap small hydrophilic molecules, small hydrophobic molecules and macromolecules. In each of these examples, an encapsulation efficiency of approximately 60% to approximately 80% may be achieved. The nanoparticles formed in accordance with the present invention may be able to provide sustained delivery of the encapsulated molecule for up to a week, or possibly more, in an in vitro and in vivo environment.

In one aspect of the invention, methods are employed to produce therapeutic and/or diagnostic nanoparticles, e.g., an anticancer agent-containing nanoparticles. Such nanoparticles can provide targeted delivery and temporal control of the release of an active agent, which is often a therapeutic agent such as a small molecular drug, nucleic acids, protein, vaccine, antibody, chemical or other agent or substance. In addition to the therapeutic methods described, the invention provides means for producing nanoparticles with diagnostic moieties, e.g., imaging agents, probes, and the like.

In a further aspect of the invention, a kit is provided for preparation of nanoparticles in accordance with the methods of the invention. The kit contains a selected amount of a water-soluble protein, at least one buffering agent and at least one surfactant. The kit may also include a hydroalcoholic solvent. The kit may also include at least one phospholipid the amount of which may be selected to provide a selected ratio of phospholipids to surfactant.

BRIEF DESCRIPTION OF THE FIGURES

FIG. 3(a) is a scanning electron microphotograph of blank zein nanoparticles. The particles are shown to be spherical and with a smooth surface. (Scale represents 1 mm=1.76 μm.) FIG. 3(b) is a transmission electron microphotograph of blank zein nanoparticles. (Scale represents 1 mm=8.038 nm.) FIG. 3(c) is a scanning electron microphotograph of coumarin-loaded zein nanoparticles. (Scale represents 1 mm=0.87 μm). FIG. 3(d) is a transmission electron microphotograph of 6,7 hydroxy coumarin-loaded zein nanoparticles. (Scale represents 1 mm=8.04 nm.)

DETAILED DESCRIPTION OF THE PREFERRED EMBODIMENTS

Figure 1:
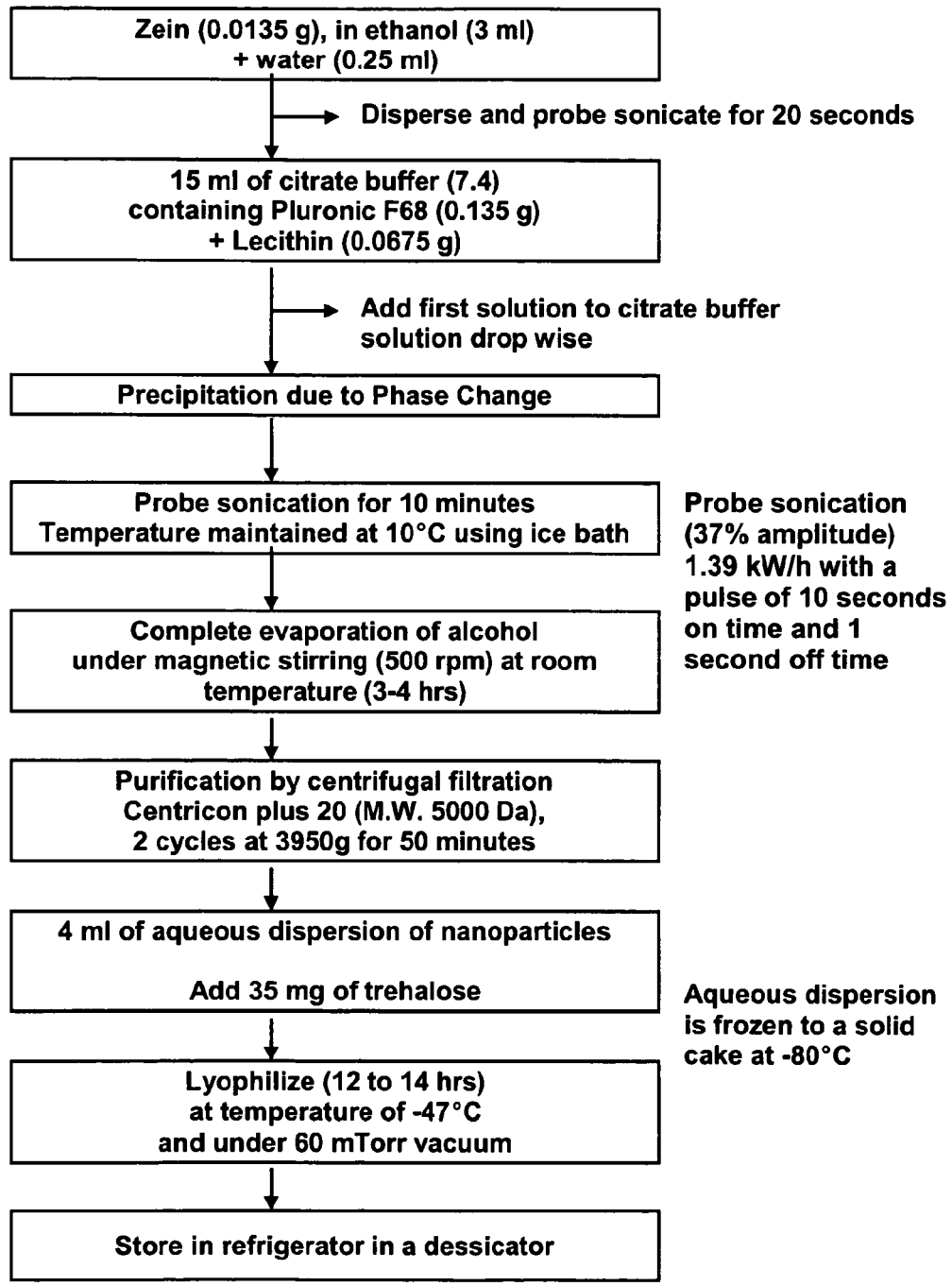
FIG. 1 illustrates by means of a flow chart the general steps of forming blank zein nanoparticles in accordance with the method of the present invention.

As used herein, the term "nanoparticle" is generally known to refer to a particle that is not more than 1000 nm in at least one dimension. However, the nanoparticles formed by the methods of the present invention will have a diameter of a specified value as defined herein. Further, the use of the term "nanoparticle" is also meant to refer generically to blank nanoparticles and nanoparticles loaded with a molecule and formed by methods of the present invention.

As used herein, unless defined otherwise (i.e., FIG. 18), "blank nanoparticle" refers to and means nanoparticles formed in accordance with the methods of the invention that do not have a selected particle, molecule or material formed with or in conjugation with the nanoparticle.

As used herein, the term "diameter," when used in the context of nanoparticle dimensions, refers to the mean linear dimension of the particle for lines passing through the center of mass of the particle. Acceptable approximation of the diameter of non-spherical particles may be provided, for example, by taking the mean of the thickness of the particle along three orthogonal axes of a coordinate system, with one of the axes aligned with the longest dimension of the particle.

As used herein, the term "administered" or "administration," when used in the context of therapeutic and diagnostic uses for nanoparticles, refers to and includes the introduction of a selected amount of nanoparticles into an in vivo or in vitro environment for the purpose of, for example, delivering a therapeutic agent to a targeted site.

As used herein, "in vivo" means of or within the body of a subject, such as that of a patient, and includes administration of nanoparticles by a variety of means including, but not limited to, oral, intravenous, intraperitoneal, parenteral, subcutaneous, topical, opthomogical and nasal routes of administration.

As used herein, "in vitro" means or refers to environments outside of the body of a subject or patient.

As used herein, the terms "subject" or "patient" both refer to or mean an individual complex organism, e.g., a human or non-human animal.

As used herein, "grades of zein" refers to a variety of types or forms of zein, including white zein and yellow zein, derived by various means, such as is disclosed in U.S. Pat. No. 5,254,673, the contents of which are incorporated herein [9].

As used herein, the term "therapeutic agent," and similar terms referring to a therapeutic or medicinal function mean that the referenced molecule, macromolecule, drug or other substance can beneficially affect the initiation, course, and/or one or more symptoms of a disease or condition in a subject, and may be used in conjunction with nanoparticles in the manufacture of medicaments for treating a disease or other condition.

As used herein, the term "biocompatible" means that the nanoparticle produced by the disclosed method of the invention does not cause or elicit significant adverse effects when administered in vivo to a subject. Examples of possible adverse effects include, but are not limited to, excessive inflammation and/or an excessive or adverse immune response, as well as toxicity.

As used herein and in the appended claims, the singular forms, for example, "a", "an", and "the," include the plural, unless the context clearly dictates otherwise. For example, reference to "a nanoparticle" includes a plurality of such nanoparticles, and reference to a "molecule" is a reference to a plurality of molecules, and equivalents thereof.

As used herein, "about" or "approximately" means reasonably close, to or a little more or less than, the stated number or amount.

As used herein, "comprising," "including," "having," "containing," "characterized by," and grammatical equivalents thereof, are inclusive or open-ended terms that do not exclude additional, unrecited elements or method steps, but also include the more restrictive terms "consisting of" and "consisting essentially of."

The present invention relates to methods of producing non-immunogenic nanoparticles from hydrophobic water-insoluble proteins by controlling the particle size of the nanoparticles within a size range of approximately 100 nm to 400 nm, and most suitably within a size range of between approximately 100 nm and 300 nm. FIG. 1 illustrates by means of a flow chart the general steps of preparing non-immunogenic nanoparticles by the method of the present invention.

In an initial step or phase of the method, a water-insoluble protein (0.4 to 1.25% w/v) is dissolved in a hydroalcoholic solvent that may contain ethanol and deionized water. The composition of the solvent may be 90:10% v/v or 92:8% v/v, for example. For methods where a selected molecule is to be encapsulated in the nanoparticle, the molecule (0.03 to 0.3% w/v) to be encapsulated is added to the solution of this first aqueous phase. The molecule to be encapsulated is approximately 5 to 50% w/w of the protein polymer.

The pH of the solution may be altered to bring the pH of the solution to between about pH 6 and about pH 7 by the addition of 0.01NaOH or 0.01N HC. If the water pH changes after addition of an acidic molecule, such as coumarin, or by a basic molecule, the pH is to be adjusted to pH 6 to 7. The solution of the first phase may be processed by probe sonication to aid is the dissolution of the protein.

In a subsequent step of the method, the aqueous solution of the initial step or phase is added to a buffering agent under ultrasonic shear. Citrate buffer is particularly preferred. The choice of the buffering agent utilized for the second aqueous phase is considered to be significant for maintaining the pH during nanoparticle formation, and is also significant for subsequent lyophilization of the formed nanoparticles as described later in this disclosure. If no buffer is used, or if, for example, 0.1N HCl is used to adjust the pH of the second aqueous phase solution, the particles produced tend to be larger than those produced with the citrate buffer, and the particles tend to demonstrate a wider size range. Use of a citrate buffer produces some of the smallest particle diameter sizes, such as approximately 100 nm. Use of other buffers may produce particles in the same or similar diameter size range of approximately 100 nm to approximately 300 nm, but after the lyophilization step, the size of the nanoparticles formed using other buffering agents tends to increase by two to three times.

Significantly, the pH of the second aqueous phase solution is preferably between approximately pH 6.8 and approximately pH 7.4 to obtain the desired size of nanoparticles. If the pH is outside of this range, the particle size tends to become larger, and the polydispersity index (PDI) of the particles produced is higher. The PDI is a measure of the distribution of the particles in different size ranges. The method thus may utilize the solubility difference of a protein, such as zein, in the hydroalcoholic solution and an aqueous solution with a selected pH of approximately 6.8 to approximately 7.4 close to the isoelectric point of zein.

Further, the addition of a buffering agent to the second aqueous phase solution may be performed under high ultrasonic shear or under high pressure homogenization, or a combination of both ultrasonic shear and high pressure homogenization. The ultrasonic energy and duration of ultrasonic shear may be particularly significant to the formation of particles in the desired diameter size ranges. The ultrasonic shear energy may be carried out from 0.6 kW/h to 1.39 kW/h, for a duration of approximately 2 to 10 minutes with a pulse on-time of from 5 to 10 seconds and an off-time of from 1 to 5 seconds. The ultrasonic processing may be significant to the production of particles in the desired size range. When employing high pressure homozenization, the process may be carried out using an orifice size of between 0.1 mm and 0.25 mm, and for a time period of between five to ten minutes at a pressure of from 5000 to 40,000 psi.

The buffering agent of the second phase may also preferably contain a surfactant and a phospholipid in a selected ratio. The ratio of surfactant to phospholipid may be approximately 2:1% w/w, which is believed to produce the most desirable results. The ratio may also be 1:0.5% w/w or 1:1% w/w or 1:2% w/w. Significantly, the utilization of the combination of a surfactant and a phospholipid is highly desirable to stabilize the particles produced and to help prevent aggregations of the particles. By way of example only, the surfactant may be a poloxamer, such as Pluronic® F68, and the phospholipid may be lecithin. Other surfactants that may be used in the method include other nonionic surfactants such as poloxamers (Pluronic®), polyoxyethylene alkyl ethers (Brij), sorbitan esters (Span), polyoxyethylene sorbitan fatty acid esters (Tween), and ionic surfactants such as sodium dioctyl sulfosuccinate, sodium lauryl sulfate, benzalkonium chloride, cetyl trimethyl ammonium bromide, n-dodecyl trimethyl ammonium bromide, and polymer such as polyvinyl alcohol, polyvinyl pyrrolidone. Other phospholipids that may be used in the method include non-ionic and charged lipids or phospholipids such as egg lecithin, soy lecithin, phosphatidyl choline, phosphatidyl ethanolamine, 1,2-dioleoyl-3-trimethyl ammonium propane.

A combination of poloxamer and lecithin (e.g., 0.9% w/w: 0.45% w/w) in the selected ratio has been found to produce nanoparticles in the desired diameter size range of approximately 100 nm to approximately 300 nm. Use of either of the surfactant or phospholipid alone has generally been found to result in larger particle sizes outside of the desired diameter size range. However, the use of either a surfactant or a phospholipid in accordance with the methods disclosed herein will result in nanoparticles of a desired size for non-immunogenicity.

After the application of ultrasonic shear or/or high pressure homozenization to the solution of the second phase, the mixture may be stirred to evaporate the ethanol or other solvent to form the nanoparticles. The stirring may be performed by a mechanical stirrer, and may be performed at a rate of from approximately 300 rpm to approximately 500 rpm at room temperature for approximately three hours.

The nanoparticles may preferably then be subjected to ultracentrifugal filtration for the purpose of separating the nanoparticles from the residual material. Ultracentifugation may be carried out using centrifugal filters of molecular weight cut-off of about 5000 Da (or other appropriate filters with a higher or lower Mwt cut-off than 5000 Da), and at between 2000 g and 40,000 g, depending on the encapsulated molecule or drug, or on the particular treatment of the nanoparticles, such as PEGylation. The time of the ultracentrifugation can vary from between 20 and 50 minutes.

A cryoprotectant may then be added to the nanoparticles. For example, 2% w/v trehalose may be added as a cryoprotectant. Other cryo- or lyo-protectants can also be used, such as sugars, including glucose, sucrose, lactose, ficoll, betaine or mannitol or poyols such as mannitol, sorbitol, which can be used as lyoprotectants. The nanoparticles may be kept at –80° C. to form a solid cake, which is then lyophilized, such as by drying the nanoparticles in a frozen state under high vacuum. The duration of ultrasonic energy, type of surfactant, concentration of surfactants, and buffer may be varied.

By way of example, nanoparticles having a size range distribution of between approximately 100 nm and approximately 400 nm were prepared as follows:

Example I

In a first aqueous phase, 0.0135 g of white zein was dissolved in a mixture of 3 ml of ethanol and 0.25 ml of water. The concentration of zein or solvent combination used was optimal; however, nanoparticles in the desired different size range can be produced by modifying the zein concentration or solvent composition. Dissolution of the zein was aided by the application of probe sonication for about 20 seconds. The resulting solution of the first aqueous phase was then added drop-wise into a 15 ml solution of citrate buffer, with a pH 7.4, and a combination of lecithin (0.45% w/v) and Pluronic® F68 (0.9% w/v) under constant application of ultrasonic energy (1.39 kW/h, 37% amplitude) for 10 minutes with a pulse on time of 10 seconds and off time of 1 second. During the ultrasonic shearing process, the dispersion was kept in an ice bath to maintain the temperature at about 10° C. The dispersion was then placed on a magnetic stirrer at between 300 to 500 rpm, at room temperature, until the ethanol was completely evaporated. After complete evaporation of the ethanol, the nanoparticles were purified to remove any residual materials and/or surface active agents. Purification was accomplished by repeated washing with deionized pH 7.4 citrate buffer and ultracentrifugation using centrifugal filters of MWt cut off of 5000 Da, at 3950 g for 50 minutes. To 4 ml of the resulting aqueous suspension (pH 7.4 citrate buffer) of zein nanoparticles was added 2% w/v trehalose as a cryoprotectant, and the nanoparticles were then kept at –80° C. to form to a solid cake. The material was then lyophilized at –47° C. and at 60 mTorr vacuum for 12 to 14 hrs. The nanoparticles were then stored in a refrigerator at 10° C. in a dessicator.

In an alternative method of the invention, the ultrasonic shear of the second phase solution can be supplemented or replaced by high pressure homogenizer by passing the dispersion under high pressure through a narrow orifice for reducing the particle size. This is especially useful to produce nanoparticles in the smaller size range when a high concentration of zein is used. Also high pressure homogenization can be used as a scale-up method for preparing zein nanoparticles. An example of the method is described below.

Example II

An amount of 0.65% w/v white zein was dissolved in a mixture of 6 ml of ethanol and 0.50 ml of water. The composition of the resulting solution of the first aqueous phase was altered to obtain a desired pH of about pH 6 to about pH 7. Dissolution of the zein was aided by the application of probe sonication for about 20 seconds. The resulting solution of the first aqueous phase was then added drop-wise into a 30 ml solution of citrate buffer, having a pH 7.4, and a combination of lecithin (0.45% w/v) and Pluronic® F68 (0.9% w/v) under constant application of ultrasonic energy (1.39 kW/h, 37% amplitude) for 2 minutes with a pulse on time of 10 seconds and off time of 1 second. During the ultrasonic shearing process, the dispersion was kept in an ice bath to maintain the temperature at about 10° C. The resulting coarse suspension was then passed through a high pressure homogenizer (Nano Debee®, USA) having an orifice size of between 0.1 and 0.25 mm for five minutes at 20,000 psi. During the high pressure homogenization process the temperature of is maintained at approximately 10° C. by circulating water in the high pressure homogenizer using a chiller. Subsequently, the dispersion was kept on a magnetic stirrer at 300 to 500 r.p.m and at room temperature until the ethanol was completely evaporated. After complete evaporation, the nanoparticles were purified to remove any residual materials or surface active agents. Purification was accomplished by repeated washing with pH 7.4 citrate buffer and ultracentrifugation using centrifugal filters of MWt cut off of 5000 Da, at 3950 g for 50 minutes. Four milliliters of aqueous suspension (pH 7.4 citrate buffer) of nanoparticles was mixed with 35 mg of 2% w/v trehalose, and was kept at –80° C. to form a solid cake. The cake was then lyophilized at –47° C. and 60 mTorr vacuum for 12 to 14 hrs.

Figure 2:
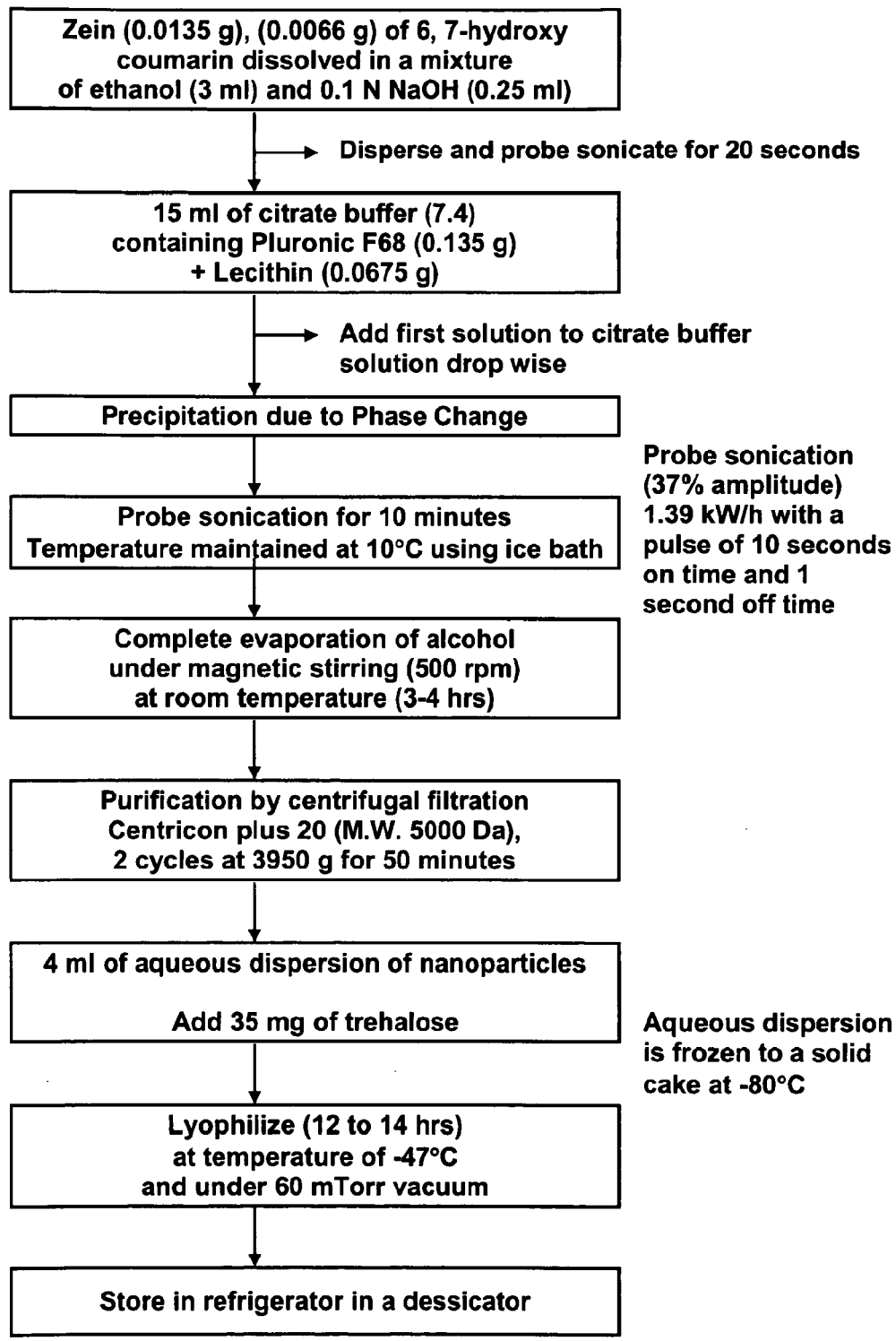
FIG. 2 illustrates by means of a flow chart the steps of forming 6,7 hydroxy coumarin-loaded nanoparticles in accordance with the invention.

The methods of the invention described in Examples I and II can be adapted for the formation of nanoparticles where a selected molecule, such as a therapeutic drug, is encapsulated within a nanoparticle (FIG. 2). An example of a method of the invention for forming a molecule-encapsulated nanoparticle is as follows:

Example III

White zein in the amount of 0.0135 g was dissolved in a mixture of 3 ml ethanol and 0.25 ml of 0.01 N NaOH to adjust the pH between 6 and 7. To the solution was added 0.0066 g of 6,7-hydroxy coumarin and the mixture was subjected to probe sonication for 20 seconds to assure dissolution. The resulting solution was added drop-wise into 15 ml of citrate buffer (pH 7.4) containing 0.0675 g of lecithin and 0.135 g of Pluronic® F68 under constant ultrasonic energy at 1.39 kW/h and 37% amplitude for 10 minutes, with a pulse on-time of 10 seconds and an off-time of 1 second. During the sonication process, the solution was kept in an ice bath to maintain the temperature around 10° C. Subsequently, the dispersion was placed on a magnetic stirrer at 300 to 500 r.p.m and at room temperature until the ethanol was completely evaporated. Following complete evaporation of the alcohol, the nanoparticles were purified to remove any excess drug and/or surface active agents. Purification was accomplished by repeated washing with pH 7.4 citrate buffer and ultracentrifugation using a centrifugal filter of MWt cut off of 5000 Da, at 3950 g for 50 minutes. Four milliliters of the aqueous suspension (pH 7.4 citrate buffer) of coumarin-loaded nanoparticles were added with 35 mg of trehalose and was kept at −80° C. to form a solid cake. The solid cake was then lyophilized at −47° C. and 60 mTorr vacuum for 12 to 14 hrs.

Figure 3:
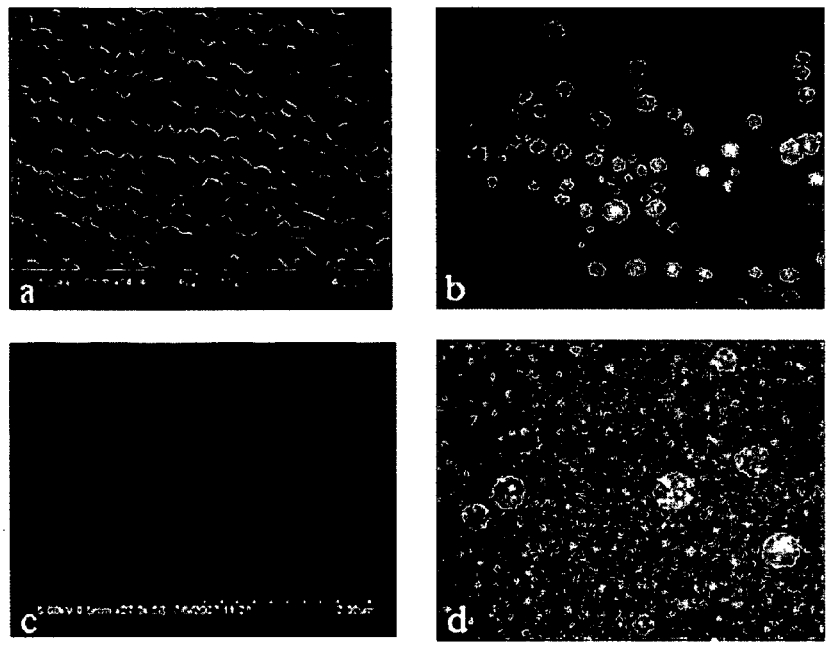
FIG. 3 depicts various electron microscopy microphotographs of zein nanoparticles.
Figure 4:
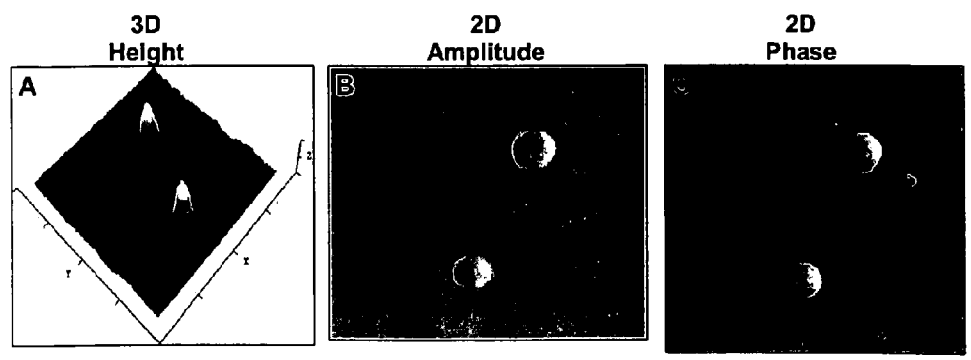
FIG. 4 depicts atomic force microscopy (AFM) images of blank zein nanoparticles produced in accordance with the methods of the invention in the tapping mode in air. Left to right are height, amplitude, and phase images of a representative sample with z-scale of 14.19 nm, 22.2 V, and 45°, respectively. The scan size is a 1.14×1.14 μm. The average particle size among 50 particles measured in AFM is 185 nm.

It has been shown that white zein may be suitably used in the methods of the present invention as the base protein. White zein gives reproducible nanoparticles in a desired narrow size range of approximately 100 nm to approximately 400 nm, while yellow zein gives larger particles with wider particle size distribution. This difference is illustrated in Table 1 and Table 2, below. Table 1 provides data of nanoparticles made from yellow zein by the method of Example I and Example III, above. Both blank and coumarin-loaded nanoparticles are shown. It can be seen that the particle size of each is approximately 460 nm and 610 nm, respectively. By comparison, as shown in Table 2, below, blank and coumarin-loaded nanoparticles made from white zein by the method of Example I and Example III are smaller. FIGS. 3 and 4 show electron microscopic and atomic force image of the blank and coumarin-loaded zein nanoparticles.

TABLE 1

| Model compound | Particle Size (nm) | Polydispersity index (PDI) | Zeta Potential (mV) | Encapsulation Efficiency (%) |
|---|---|---|---|---|
| Blank zein nanoparticles | 460 ± 63 | 0.46 ± 0.06 | −10.28 ± 2 | Not applicable |
| 6,7 Hydroxy coumarin | 610 ± 123 | 0.62 ± 0.08 | −16.28 ± 3 | 98 ± 1.5 |

Each value is an average of three experiments with ±SD.

TABLE 2

| Model compound | Particle Size (nm) | Polydispersity index (PI) | Zeta Potential (mV) | Encapsulation Efficiency (%) |
|---|---|---|---|---|
| Blank zein nanoparticles | 224 ± 20 | 0.31 ± 0.06 | −16 ± 3 | Not applicable |
| 6,7 Hydroxy coumarin | 266 ± 30 | 0.44 ± 0.08 | −11.34 ± 1.8 | 62 ± 17 |

Each value is an average of three experiments with ±SD.

The pigments in yellow zein appear to affect the solubility of zein and the formation of nanoparticles of the desired size distribution. It has been found in the prior art to be particularly challenging to prepare particles using natural polymers, such as proteins, that are consistently within the desired size range. However, the present invention can produce nanoparticles consistently in the desired size range using a suitable grade of protein, such as white zein.

Significantly, the methods of the invention may produce, and have produced, nanoparticles with a diameter size as low as 80 nm to 100 nm. If part of the ultrasonic shear is replaced by high pressure homogenization, as described in Example II, above, the resulting particle size of blank nanoparticles is also similar to the particle sizes shown in Table 2, above, namely having a particle size of approximately 220±15 nm and a PDI of 0.4±0.07.

The yield of nanoparticles produced by the nanoprecipitation methods of the present invention that are in the desired size range has been found to be greater than approximately 60%. The methods are significant in that the particles produced have diameters that primarily measure in a range of less than approximately 400 nm, and preferably with a relatively narrow diameter size distribution of approximately 100 nm to approximately 300 nm to avoid an immunogenic reaction when administered into the body. Advantageously, zein nanoparticles in the diameter size range of approximately 100 to approximately 400 nm, such as are produced by the methods of the invention, are not taken up by phagocytic cells, while larger particles of a diameter size greater than approximately 400 nm are rapidly taken up by phagocytic cells when tested in vitro using porcine blood. This suggests that nanoparticle phagocytosis is avoided by controlling the particle diameter size of zein nanoparticles in the smaller size range.

Immunogenicity studies in mice showed that zein nanoparticles in the diameter size range of approximately 100 to approximately 400 nm are non-immunogenic, while zein nanoparticles having a diameter size greater than approximately 400 nm produced a significant immune response (anti-zein antibodies were two- to four-fold higher compared to saline control). These results show that preparing and using nanoparticles having diameter sizes less than approximately 400 nm helps avoid any significant immunogenicity caused by the hydrophobic proteins of the particles.

The ability to control size of the nanoparticles is achieved in part by controlling the pH of the solution in the second aqueous phase of the method. The data in Table 3, below, illustrates that smaller sizes of nanoparticles, with a lower PDI, are achieved at a pH of between 6.8 and 7.4.

TABLE 3

| pH of the aqueous phase | Particle Size (nm) | Polydispersity index |
|---|---|---|
| 1.5 | 362 ± 24 | 0.392 |
| 3 | 291 ± 15 | 0.45 |
| 6.8 | 208 ± 10 | 0.289 |

TABLE 3-continued

| pH of the aqueous phase | Particle Size (nm) | Polydispersity index |
|---|---|---|
| 7.4 | 232 ± 7 | 0.260 |
| 10 | 256 ± 20 | 0.317 |
| 12 | 368 ± 10 | 0.438 |

Each value is an average of three experiments with ±SD

A further critical factor in controlling the size of nanoparticle formation is the combination of surfactant and phospholipids which is required to stabilize the nanoparticles and prevent particle aggregation. A combination of a poloxamer and lecithin, such as in a 2:1 ratio (e.g., 0.9:0.45% w/w), produces nanoparticles in the desired size range. If either the surfactant or the phospholipid is used alone, larger particles are obtained, as suggested by the data of Table 4, below.

TABLE 4

| Surfactant (% w/v) | Particle size (nm) | PDI |
|---|---|---|
| Pluronic ® (0.9) | 516 ± 75 | 0.57 ± 0.07 |
| Lecithin (0.9)* | 335 ± 45 | 0.52 ± 0.05 |
| Pluronic ® (0.9) and Lecithin (0.4) | 274 ± 36 | 0.46 ± 0.02 |

Each value is an average of three experiments with ±SD.
*Lyophilization resulted in a sticky powder.

Figure 5:
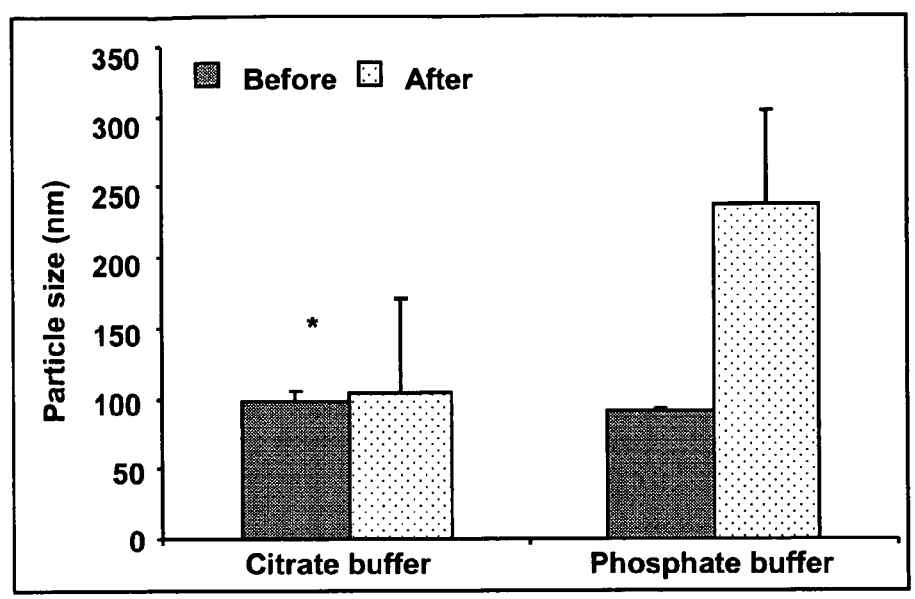
FIG. 5 is a graph illustrating the influence of buffer type on the particle size of coumarin-loaded zein nanoparticles made in accordance with the methods of the invention before and after lyophilization. Use of citrate buffer in the precipitation method of the present invention produces consistently smaller sizes of nanoparticles following lyophilization as compared with the use of phosphate buffer. (*p<0.05). Each point on the graph represents the mean±SD (n=3). Citrate buffer was composed of citric acid (0.0153 g/L) and sodium citrate (2.91 g/L) in deionized water. Phosphate buffer was composed of dibasic sodium phosphate (1.44 g/L), monobasic potassium phosphate (0.25 g/L) and sodium chloride (10 g/L) in deionized water. Both buffers were used to maintain the second aqueous phase at pH 7.4 in accordance with the invention.

The choice of buffering agent for the second aqueous phase is not only critical to maintaining the optimum pH during nanoparticle formation, but is also critical for subsequent lyophilization. For example, if no buffering agent is used in the second aqueous phase solution, or if 0.1N HCl is used to adjust the pH, the resulting nanoparticles are larger in size, with a wider size range or PDI. As shown in FIG. 5, the use of citrate buffer gave the smallest particle size (109±12 nm). The use of other buffering agents, particularly phosphate, results in the particle size of zein nanoparticles being increased by two to three times after lyophilization.

The graph of FIG. 5 illustrates that zein nanoparticles prepared by the method using phosphate as the buffering agent in the solution from the second aqueous phase and obtained after lyophilization produced much larger particles as compared to nanoparticles prepared using citrate buffer as the buffering agent in the second aqueous phase. The particle size increase in phosphate buffer is probably due to the crystallization and precipitation of buffer at the freeze-drying temperatures caused by the pH drop [10]. This problem is solved using citrate buffer, which effectively resists the changes in pH during freeze-drying temperatures. The amino groups in zein can be cross-linked by citric acid and this also stabilizes the zein nanoparticles [11].

It is notable that zein is a biodegradable protein and is also more biocompatible than synthetic polymers. Zein is a polymer that is listed as a GRAS (Generally Regarded As Safe) polymer by FDA standards [12]. The method of the invention is, therefore, suitable for preparing zein nanoparticles with encapsulated molecules or drugs of different physiochemical properties. Table 5, below, illustrates by way of example a sampling of some molecules that may be encapsulated by nanoparticles using the methods in accordance with the present invention. The number or type of molecules that may be used in the nanoparticle encapsulation are not limited to those noted herein.

TABLE 5

| Model compound | Particle Size (nm) | Zeta potential | Encapsulation efficiency (%) |
|---|---|---|---|
| 6,7-hydroxy coumarin | 173 ± 20 | −16 ± 3 | 68 ± 6 |
| Doxorubicin | 171 ± 45 | −21 ± 2 | 61 ± 16 |
| Dextran FITC (4000 Da) | 89 ± 12 | −15 ± 2 | 79 ± 8 |
| pDNA (GFP) | 185 ± 12 | −17 ± 0.4 | 86.2 ± 3 |

Each value is a mean of three experiments with ±SD.

Figure 6:
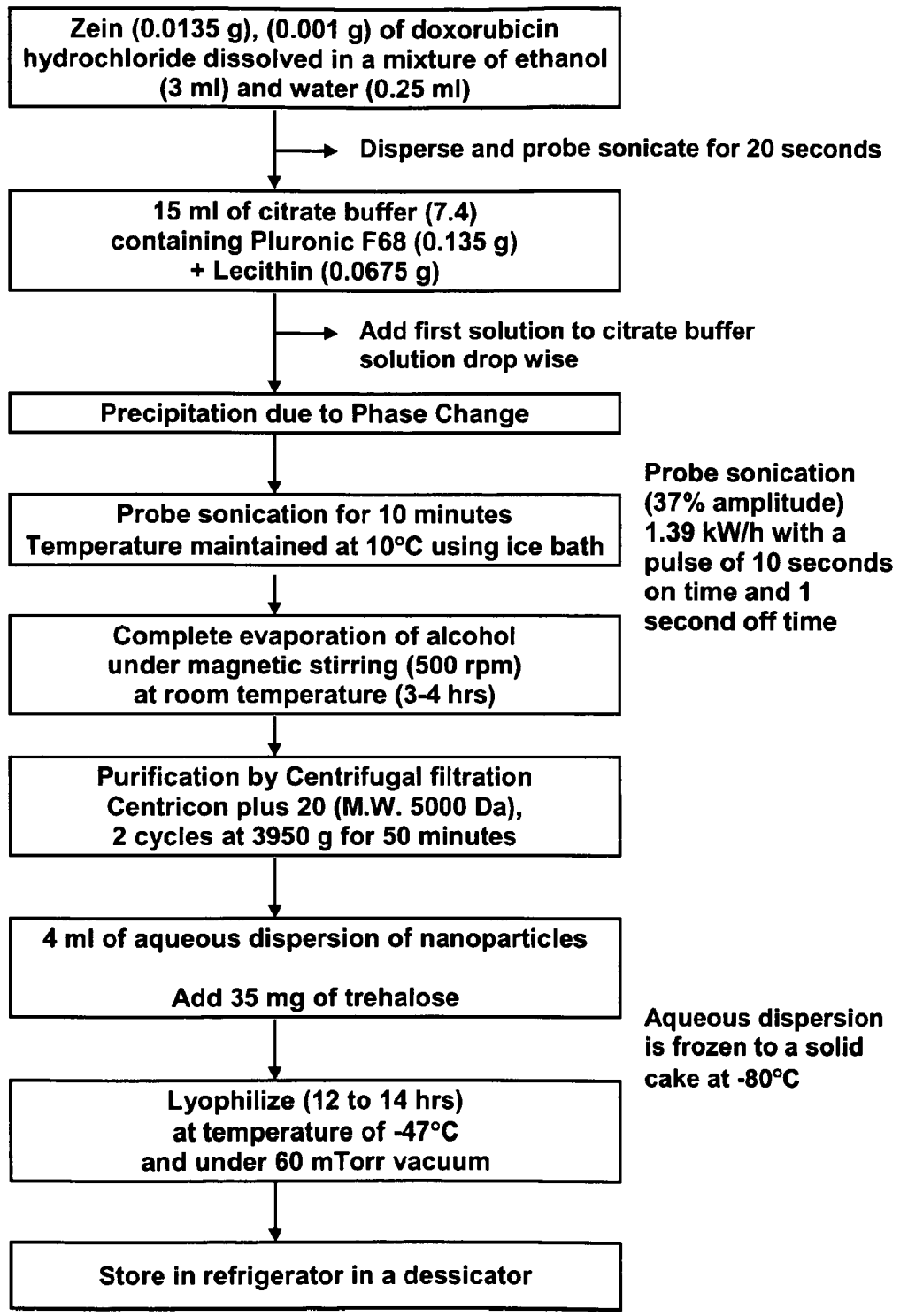
FIG. 6 illustrates by means of a flow chart the general steps of the method of the present invention for preparing doxorubicin loaded nanoparticles.

An example of a nanoparticle formed with 6,7 hydroxy coumarin is described in Example III above and is shown in FIG. 2. Another example of a nanoparticle containing a therapeutic agent is doxorubicin-loaded zein nanoparticles, the general steps of which are illustrated in FIG. 6. A specific method for preparing doxorubicin-loaded zein nanoparticles is as follows:

Example IV

White zein in the amount of 0.0135 g was dissolved in a mixture of 3 ml of ethanol and 0.25 ml of water. To this solution of the first aqueous phase was added 0.001 g of doxorubicin hydrochloride and the mixture was probe sonicated for 20 seconds to dissolve the doxorubicin hydrochloride. The resulting solution was added drop-wise into 15 ml of citrate buffer (pH 7.4) containing 0.0675 g of lecithin and 0.135 g of Pluronic® F68 under constant ultrasonic energy at 1.39 kW/h and 37% amplitude for 10 minutes with a pulse on-time of 10 seconds and off-time of 1 second. During the sonication process, the solution was kept in an ice bath to maintain the temperature at about 10° C. Subsequently, the dispersion was placed on a magnetic stirrer at 300 to 500 r.p.m at room temperature until the ethanol was completely evaporated. After complete evaporation of the alcohol, the nanoparticles were purified to remove residual material. Purification was accomplished by repeated washing with pH 7.4 citrate buffer and subjected to ultracentrifugation, using centrifugal filters of MWt cut off of 5000 Da, at 3950 g for 50 minutes. To the aqueous suspension (pH 7.4 citrate buffer) of doxorubicin nanoparticles was added 35 mg of trehalose and the mixture was kept at −80° C. to form a solid cake. The material was then lyophilized at −47° C. and 60 mTorr vacuum for 12 to 14 hrs.

In preparation of the doxorubicin-loaded zein nanoparticles according to the method (FIG. 6), particles were formed having a mean diameter of approximately 171±45 nm and a PDI of approximately 0.3. The encapsulation efficiency of doxorubicin by the zein nanoparticles was approximately 61±16%.

Figure 7:
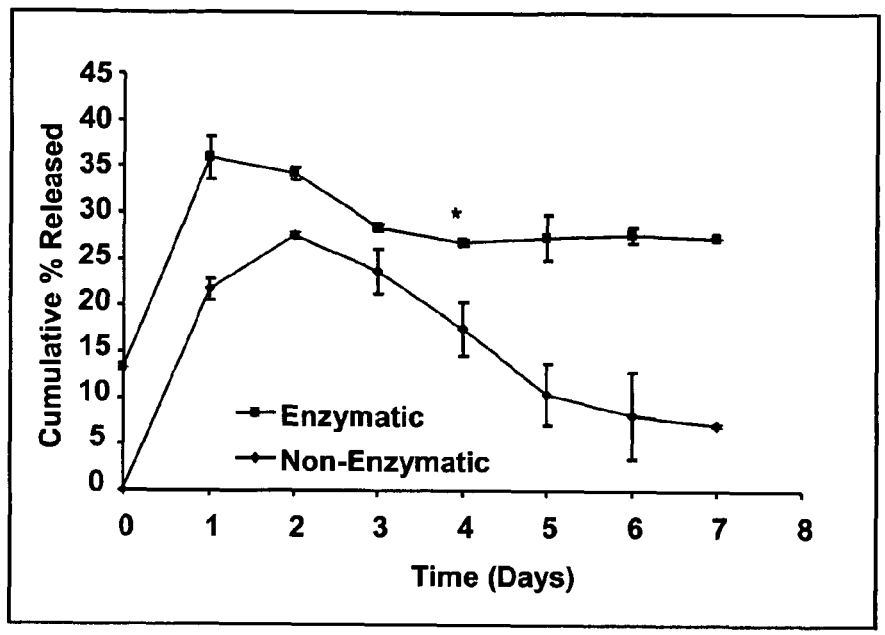
FIG. 7 illustrates an in vitro release profile of 6,7 hydroxy coumarin-loaded zein nanoparticles in phosphate buffered saline (pH 7.4). Coumarin-loaded zein nanoparticles (10 mg/ml) prepared by the method of the present invention were placed in a dialysis membrane (Spectrapor™, M.wt. 5000 Da) and incubated in phosphate buffered saline (pH 7.4) in the absence (non-enzymatic) or presence (enzymatic) of trypsin (10 mg/ml). Ethanol (20% v/v) was added to the media to maintain sink conditions, and sodium azide (0.005% w/v) was used as an anti-microbial agent. The solution was maintained at 37° C. in a horizontal shaker waterbath at 50 rpm. An aliquot (1 ml) of the dialysate was removed at different time points for 7 days and replaced with fresh media to maintain the sink conditions. Dialysate was analyzed for coumarin released from the zein nanoparticles using spectrofluorimetry ($\lambda_{ex}$=490 nm; $\lambda_{em}$=520 nm). Each data point is a mean of three experiments (±SD). Enzymatic release was higher compared to non-enymatic release at all time points (p<0.05).
Figure 8:
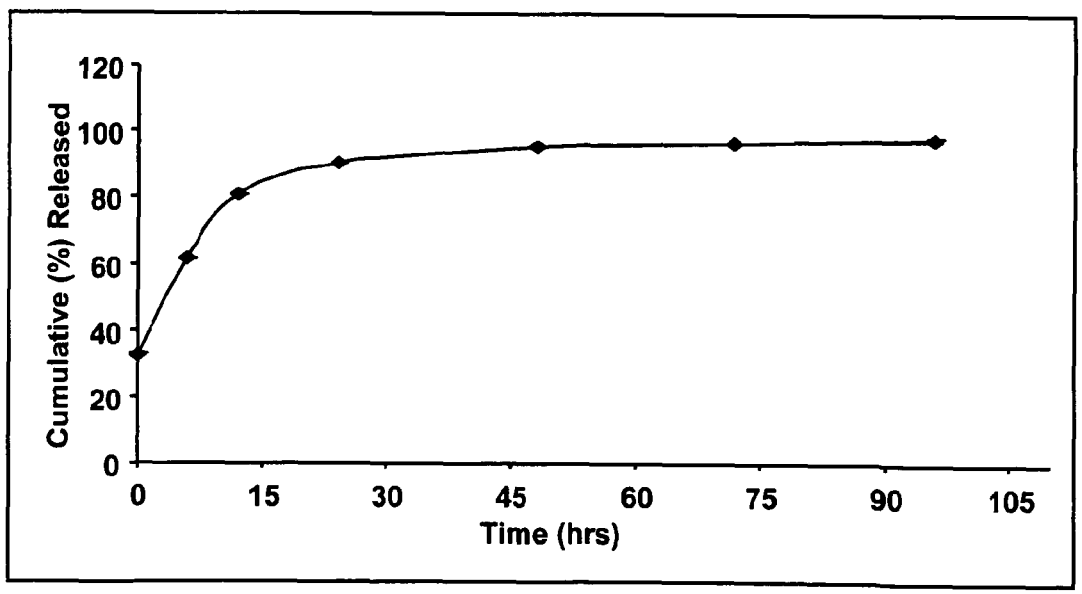
FIG. 8 illustrates the in vitro release profile of doxorubicin from zein nanoparticles in phosphate buffered saline (pH 7.4). Doxorubicin-loaded zein nanoparticles (10 mg/ml) prepared by the nanoprecipitation method of the present invention were incubated in 1 ml of phosphate buffered saline (pH 7.4) in a centrifuge tube and the solution was maintained at 37° C. in a horizontal shaker water bath at 50 rpm. The sample was centrifuged at 10,000 rpm for 10 minutes and the supernatant was analyzed for doxorubicin released from the nanoparticles using HPLC. A C-18 column was used and the mobile phase (flow rate 1 ml/min) was 0.1% TFA: Acetonitrile (acetonitrile gradient from 5 to 80% was used). A fluorescence detector ($\lambda_{ex}$=505 nm; $\lambda_{em}$=550 nm) was used to detect doxorubicin. The release study was conducted for up to four days. Each data point is a mean of three experiments (±SD).

Zein nanoparticles made in accordance with the present invention provide a beneficial and/or advantageous sustained release of the encapsulated molecule or drug due in part to the water insolubility of zein nanoparticles that enable the particles to sustain the drug release over a period of time. For example, FIG. 7 depicts the in vitro release profiles for coumarin-loaded nanoparticles made in accordance with the method described in Example II, above. The data indicates that in vitro, there is a sustained release of the drug over a period of up to seven days, with a higher release rate being observed in the presence of enzymes. The data shows that the zein nanoparticle release is mediated by slow diffusion of drug out of the nanoparticle and slow enzymatic breakdown of zein nanoparticles. FIG. 8 depicts the in vitro release profile of doxorubicin from the doxorubicin-loaded zein nanoparticles made according to Example IV, showing a mixed order with an initial burst followed by a sustained release after approximately 24 hours.

Figure 9:
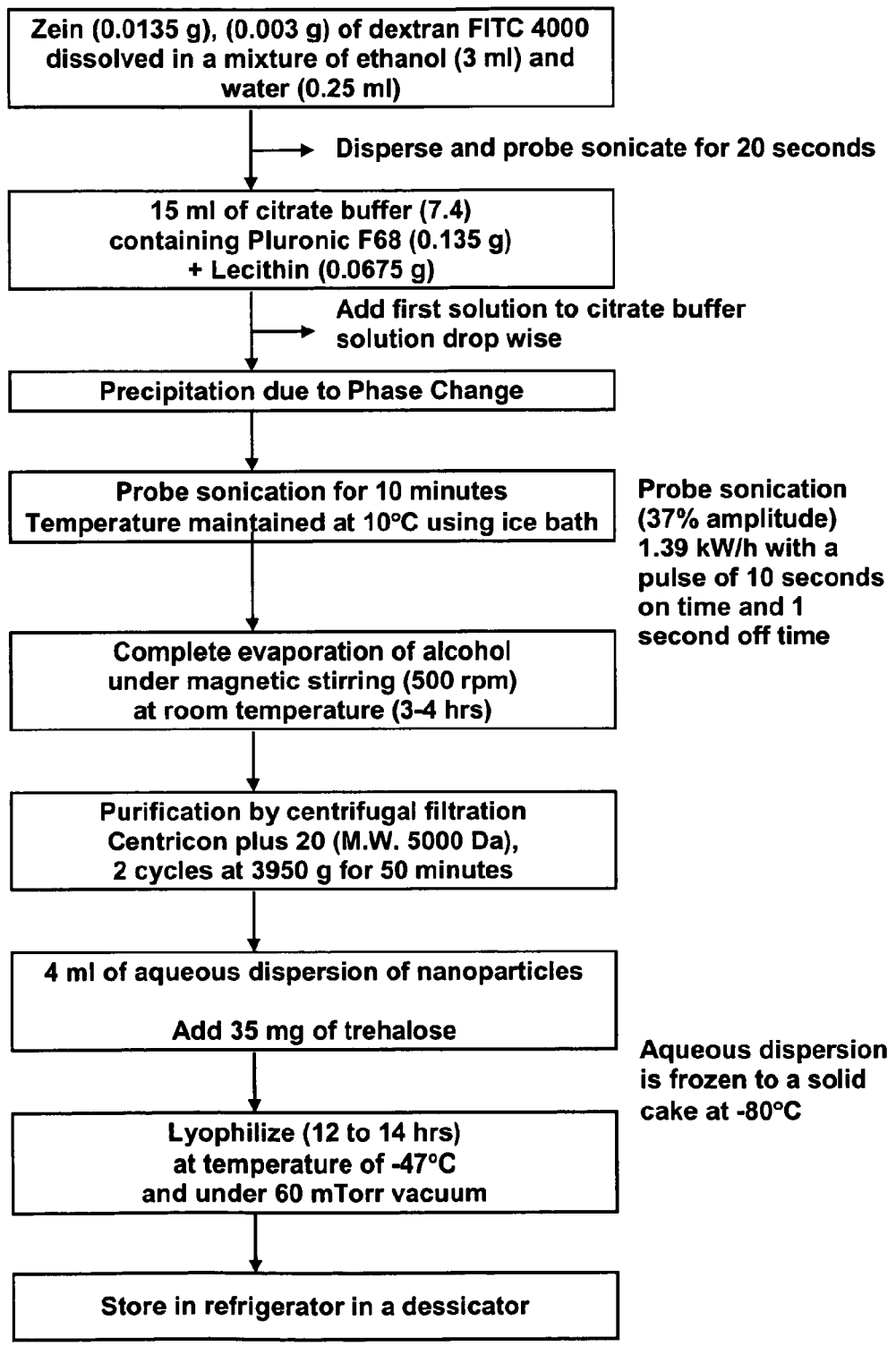
FIG. 9 illustrates by means of a flow chart the general steps of a method of the present invention for the preparation of dextran-FITC (fluoroisothiocyanate)-loaded nanoparticles. The molecular weight of dextran is 4000 Da.

A further example of a therapeutic or diagnostic agent that may be formed as a nanoparticle in accordance with the invention is Dextran-FITC (FIG. 9). An example of preparing a Dextran-FITC-loaded zein nanoparticles is as follows:

Example V

An amount of 0.0135 g of white zein was dissolved in a mixture of 3 ml of ethanol and 0.25 ml water. To the zein solution was added 0.003 g of dextran (Mwt 4000 Da) labeled with FITC and the dextran-FITC was dissolved in the above solution. The resulting solution was added drop-wise into 15 ml of citrate buffer (pH 7.4) containing 0.0675 g of lecithin and 0.135 g of Pluronic® F68 under constant ultrasonic energy at 1.39 kW/h and 37% amplitude for 10 minutes with a pulse on-time of 10 seconds and off-time of 1 second. During the sonication process, the solution was kept in an ice bath to maintain the temperature at about 10° C. Subsequently, the dispersion was placed on a magnetic stirrer at 300 to 500 r.p.m at room temperature until the ethanol was completely evaporated. After complete evaporation of the alcohol solvent, the nanoparticles were purified to remove the residual materials. Purification was accomplished by repeated washing with pH 7.4 citrate buffer and ultracentrifugation, using centrifugal filter of MWt cut off of 5000 Da, at 3950 g for 50 minutes. To the aqueous suspension (pH 7.4 citrate buffer) of dextran-FITC-loaded nanoparticles was added 35 mg of trehalose and the mixture was kept at −80° C. to form a solid cake. The material was then lyophilized at −47° C. and 60 mTorr vacuum for 12 to 14 hrs.

Figure 10:
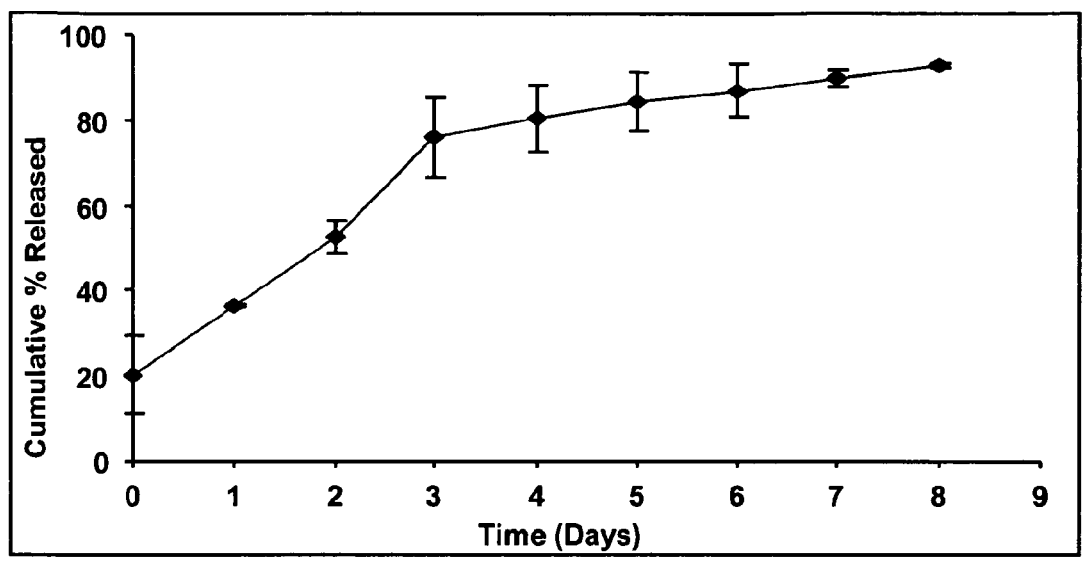
FIG. 10 illustrates an in vitro release profile of dextran-FITC from zein nanoparticles in phosphate buffered saline (pH 7.4). Dextran-FITC-loaded zein nanoparticles (10 mg/ml) were prepared by a method of the present invention, were incubated in 1 ml of phosphate buffered saline (pH 7.4) in a centrifuge tube and were maintained at 37° C. in a horizontal shaker water bath at 50 rpm. The sample was centrifuged at 10,000 rpm for 10 minutes and the supernatant was analyzed for dextran-FITC released from the nanoparticles by use of spectrofluorimetry ($\lambda_{ex}$=490 nm; $\lambda_{em}$=520 nm). The study was conducted for eight days. Each point represents the mean±SD (n=3).

Dextran-FITC nanoparticles prepared in accordance with the invention (FIG. 9) shows a sustained in vitro release profile, as shown in FIG. 10.

Figure 11:
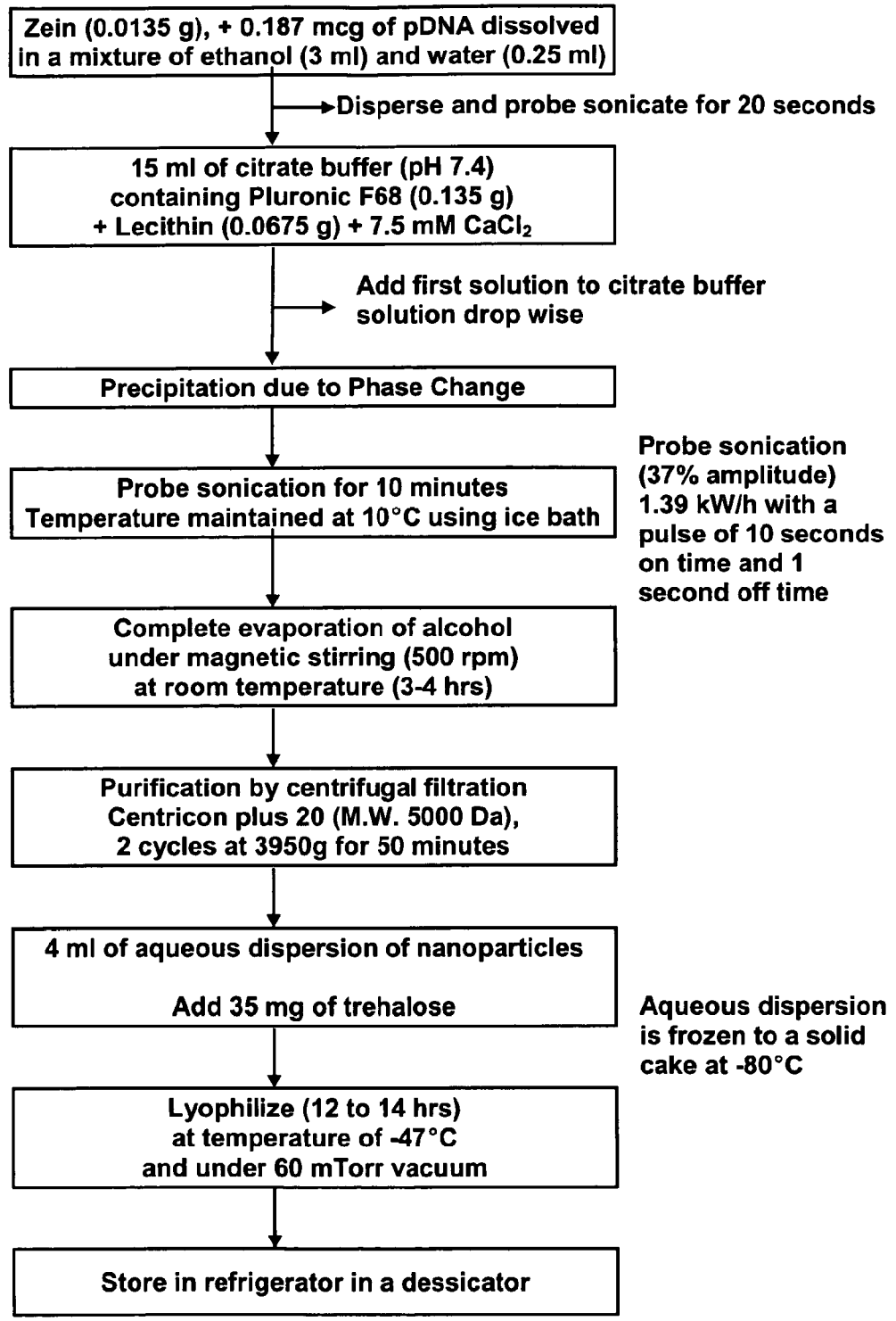
FIG. 11 illustrates by means of a flow chart the general steps of the method of the present invention for the preparation of plasmid DNA-loaded nanoparticles. The plasmid DNA (pDNA) encoding for green fluorescent protein (GFP) that was used in the study was propagated using a DH5α strain of E. coli, which was grown in LB medium. The plasmid was isolated using Qiagen's 'EndoFree Plasmid Mega Kit'. The purified pDNA was characterized using UV-spectrophotometer, by calculating the ratio of UV absorbance at 260/280 nm, and also characterized by agarose gel electrophoresis.

Further in accordance with the present invention, molecules that are suitable for gene therapies can also be encapsulate in nanoparticles for therapeutic and diagnostic use, such as, for example, plasmids, DNA, oligonucleotides and siRNA. FIG. 11 illustrates the general method for preparing a nanoparticle containing a gene-based molecule. A specific example for making a nanoparticle comprising pDNA (plasmid DNA) encapsulated in a nanoparticle is as follows:

Example VII

An amount of 0.0135 g of white zein was dissolved in a mixture of 3 ml of ethanol and 0.25 ml water. To the zein solution was added 0.187 μg of pDNA GFP (green fluorescent protein) which was dissolved in the above zein solution. The resulting solution was added drop-wise into 15 ml of citrate buffer (pH 7.4) containing 0.0675 g of lecithin, 0.135 g of Pluronic® F68 and 7.5 mM of $CaCl_2$ under constant ultrasonic energy at 1.39 kW/h and 37% amplitude for 10 minutes with a pulse on-time of 10 seconds and off-time of 1 second. During the sonication process, the solution was kept in an ice bath to maintain the temperature at about 10° C. Subsequently, the dispersion was placed on a magnetic stirrer at 300 to 500 r.p.m at room temperature until the ethanol was completely evaporated. After complete evaporation of the alcohol solvent, the nanoparticles were purified by ultracentrifugation using a centrifugal filter with a Mwt cut-off of 5000 Da and processing at 3950 g for 50 minutes to remove excess drug, and surface active agents. Two cycles of ultracentrifugation were conducted and the nanoparticles are washed with water. To the aqueous suspension of pDNA-loaded nanoparticles was added 35 mg of trehalose and the mixture was kept at −80° C. to form a solid cake. The material was then lyophilized at −47° C. and 60 mTorr vacuum for 12 to 14 hrs.

The drug release profiles for the various encapsulated molecules, as shown in FIGS. 6, 8 and 10 for example, indicate that zein nanoparticles can be used as a versatile and safe drug delivery vehicle by parenteral and non-parenteral routes of administration including oral, buccal, transdermal, nasal, pulmonary and ocular routes of delivery. Many other molecules, particles and drugs may be encapsulated as well, including but not limited to, vaccines and cosmetic substances (e.g., Minoxidil, Vitamin C, etc.) for therapeutic, diagnostic and aesthetic applications or therapies.

Figure 12:
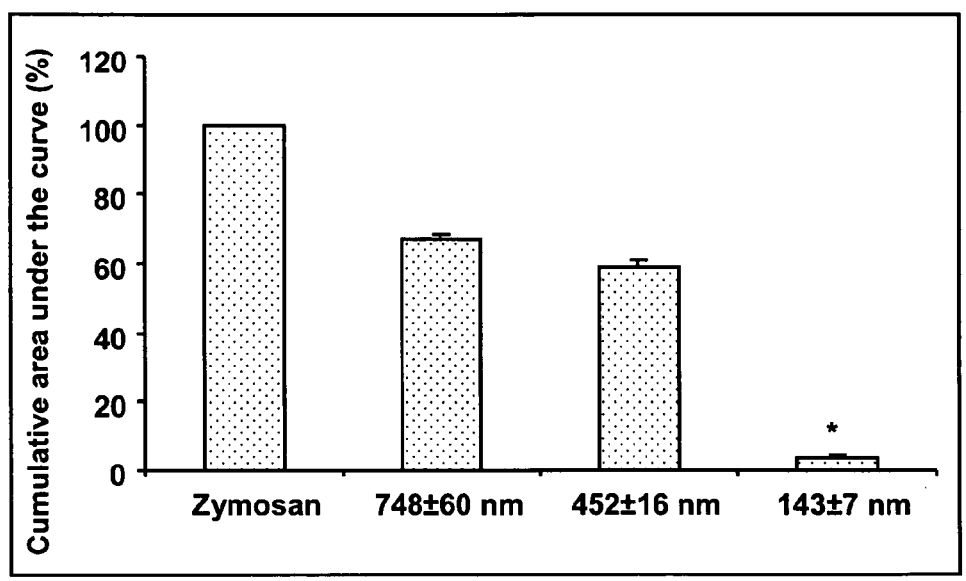
FIG. 12 illustrates the influence of particle size on uptake of zein nanoparticles by porcine polymorpho-nuclear cells. The figure shows the percent area under the curve for luminal chemiluminescence (over 90 minutes) in the presence of zein particles and positive control zymosan. Each experiment is an average of four experiments (±SEM). Uptake is significantly low in smaller particle sized (p<0.05) compared to other groups.
Figure 13:
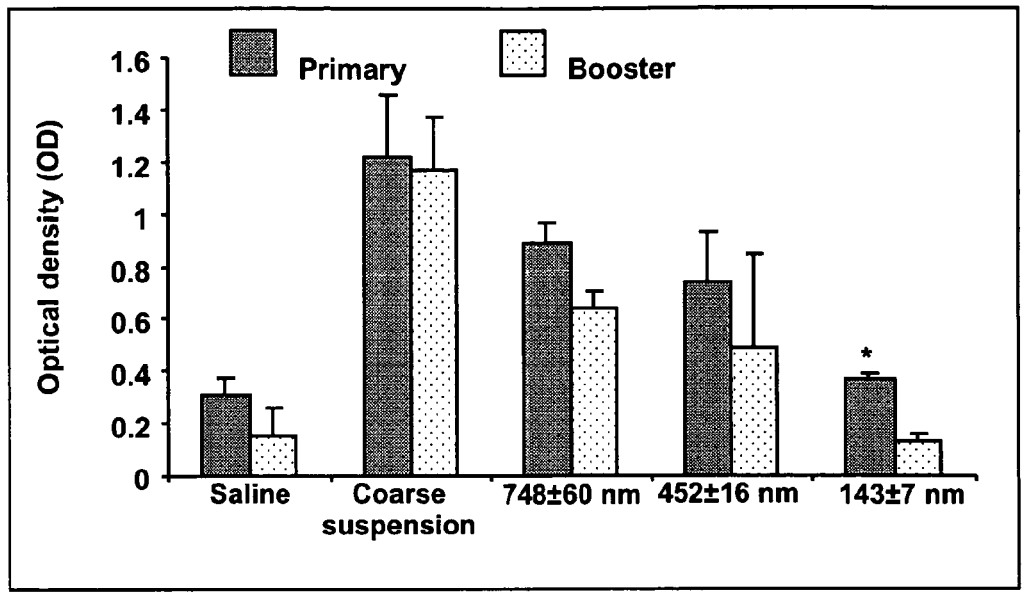
FIG. 13 illustrates anti-zein antibodies (optical density) measured after the third and fifth weeks of primary and booster subcutaneous injections of zein particles, respectively. Each value is represented as mean±SEM (n=4). Both the primary and booster titres were statistically not significant (p>0.05) compared to the saline group. A coarse zein suspension or zein particles in saline (equivalent to 100 µg/50 µl) were injected subcutaneously in female Balb/c mice. Blood was withdrawn from the orbital plexus and the anti-zein antibody levels in the diluted serum (1/16) were measured using a mouse ELISA kit.

Further, due to the relatively smaller size of the nanoparticles formed by the methods of the present invention, molecule-loaded (e.g., drug-loaded) zein nanoparticles can circulate in the body for prolonged periods without being recognized and eliminated by phagocytic cells. The data of FIG. 12 illustrate that zein nanoparticles in the size range of 100-400 nm are not taken up by the blood phagocytic cells, while larger particles in the size of >400 nm are rapidly taken up by phagocytic cells when tested in vitro using porcine blood. Thus, it can be shown that phagocytic uptake is avoided by controlling the particle size of zein nanoparticles in the smaller size range. Immunogenicity studies in mice showed that zein nanoparticles in the size range of 100 nm to 400 nm are non-immunogenic. On the other hand, zein nanoparticles having a size >400 nm produced a significant immune response (two- to four-fold) compared to the control, as shown in FIG. 13.

Figure 14:
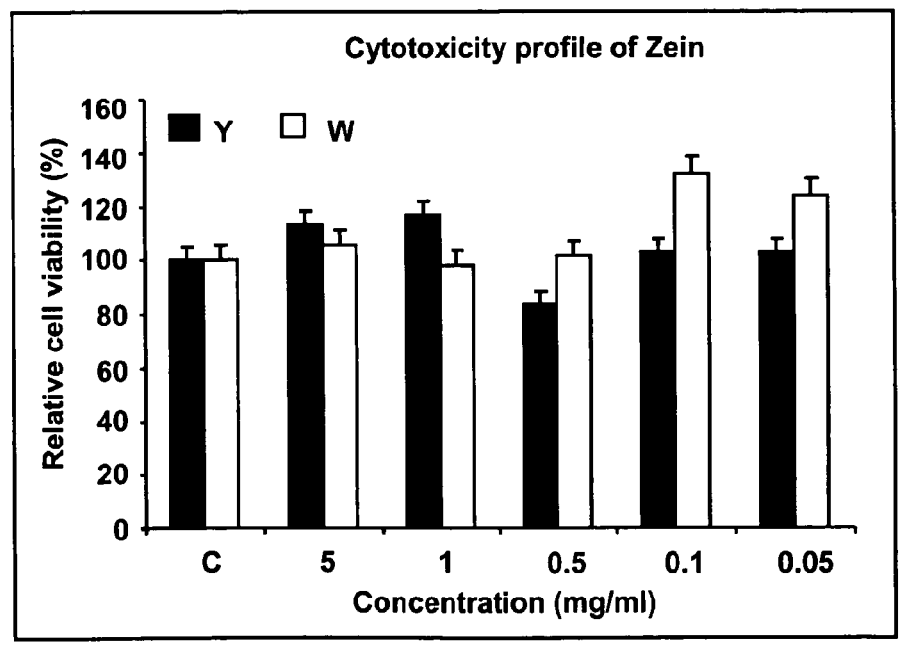
FIG. 14 is a graph illustrating the influence of yellow zein (Y) and white zein (W) on cell viability of porcine intestinal epithelial cells (IPEC-J2 cells) (at 20,000 cells/well) expressed as the relative activities of mitochondrial dehydrogenase after four hours of treatment using a dimethylthiazol-2-yl-2,5-diphenyltetrazolium bromide (MTT) assay. The plate without any treatment was used as a control and was considered to be 100% viable. Zein powder was dissolved in 55% v/v ethanol and subsequent dilutions were made from 5 mg/ml stock in serum-free media. At all concentrations, both yellow and white zein do not differ significantly from the control with no treatment (*p<0.05). Each data point is an average of three experiments±SEM.

The cytotoxic effects of the zein used for making the nanoparticles were investigated in cell proliferation studies using porcine intestinal epithelial cells (IPEC-J2). The results of an exemplary cytotoxicity studies is shown in FIG. 14. No significant degree of cytotoxicity was observed between white zein and yellow zein, as compared to control treatment with buffer at any concentration.

Figure 15:
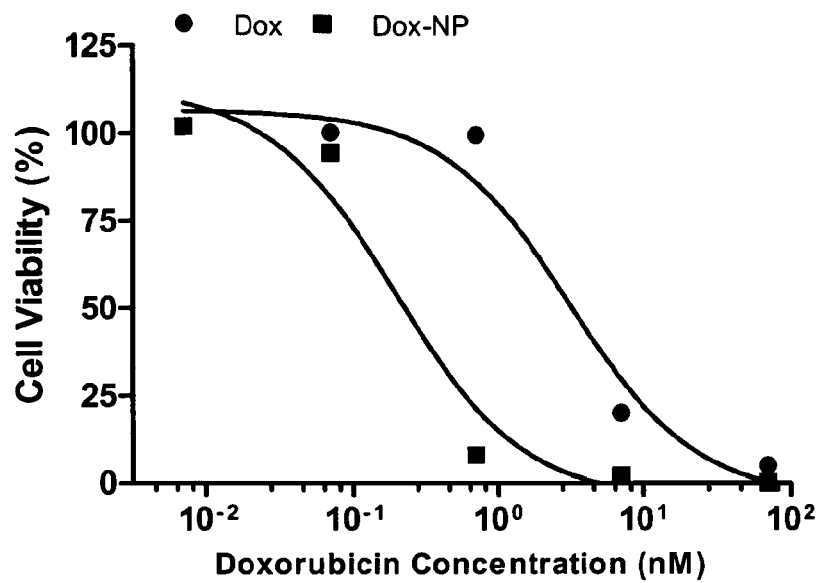
FIG. 15 illustrates an in vitro cytotoxicity profile of doxorubicin solution and doxorubicin-zein nanoparticles prepared in accordance with the invention in OVACAR-3 cells (human ovarian cancer cells). Cells were exposed to doxorubicin solution and doxorubicin-loaded nanoparticles at a concentration of 0.0001 to 10 µM for 24 hours. The drug treatment was removed after 24 hours and the cells were incubated with blank medium (medium changed every 48 hours) for five days, and the cell viability was measured on the fifth day by MTT assay. Each data point is an average of four experiments. The $IC_{50}$ for doxorubicin solution and doxorubicin-zein nanoparticles were 3.1 nM and 0.20 nM, respectively. (Dox=doxorubicin solution; Dox-NP=doxorubicin nanoparticles.)
Figure 16:
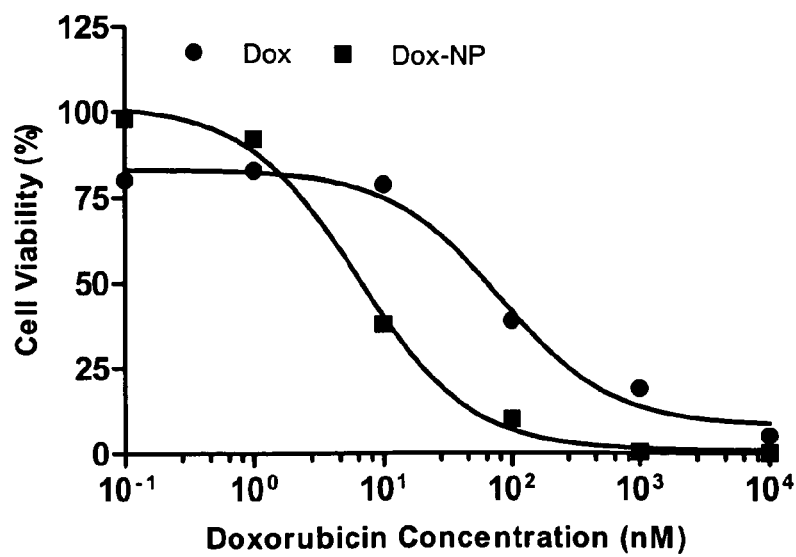
FIG. 16 illustrates an in vitro cytotoxicity profile of doxorubicin solution and doxorubicin-zein nanoparticles prepared in accordance with the invention in doxorubicin-resistant human breast cancer cells (NCI/ADR-RES cells). Cells were exposed to doxorubicin solution and doxorubicin-loaded nanoparticles at a concentration of 0.0001 to 10 µM for 24 hours. The drug treatment was removed after 24 hours and the cells were incubated with blank medium (medium changed every 48 hours) for five days, and the cell viability was measured on the fifth day by an MTT assay. Each data point is an average of four experiments. The $IC_{50}$ for doxorubicin solution and doxorubicin-loaded nanoparticles were 81.73 nM and 6.41 nM, respectively. (Dox=doxorubicin solution; Dox-NP=doxorubicin-loaded nanoparticles.)

The therapeutic activity of zein nanoparticles made in accordance with the disclosed methods was tested in vitro using doxorubicin-loaded zein nanoparticles with human ovarian cancer cells (OVCAR-3) (FIG. 15) and doxorubicin-resistant human breast cancer cells (NCI/ADR-RES) (FIG. 16). The cells were plated at a seeding density of 2000 cells/well/0.1 ml. Following overnight attachment, the cells were treated with 0.07 to 70 nM (OVCAR-3) and 0.1 to 10000 nM (NCI/ADR-RES) concentrations of either doxorubicin solution or doxorubicin-nanoparticles for 24 hours. After 24 hours, the respective drug treatments were removed. The cells were washed twice with ice cold phosphate buffer and replaced with fresh media. Media was replaced every 48 hrs. An MTT assay was used to assess cytotoxicity on the fifth day following treatment (NCI and OVCAR-3). The results show that the doxorubicin-loaded in zein nanoparticles had a significantly higher potency than the free doxorubicin solution in human cancer cells. Doxorubicin-loaded nanoparticles were approximately 12 to 16 times more potent than the free doxorubicin. The difference in potency is believed to be due to the difference in the cell uptake mechanism of free drug and drug encapsulated in nanoparticles. Free doxorubicin is taken up by passive diffusion dictated by the concentration gradient, while the doxorubicin-loaded nanoparticles are taken up in an active endocytosis process. Further it is believed that the endocytosis of doxorubicin-loaded nanoparticles can avoid the drug efflux pumps in resistant cancer cells, thus resulting in better efficacy.

Figure 17:
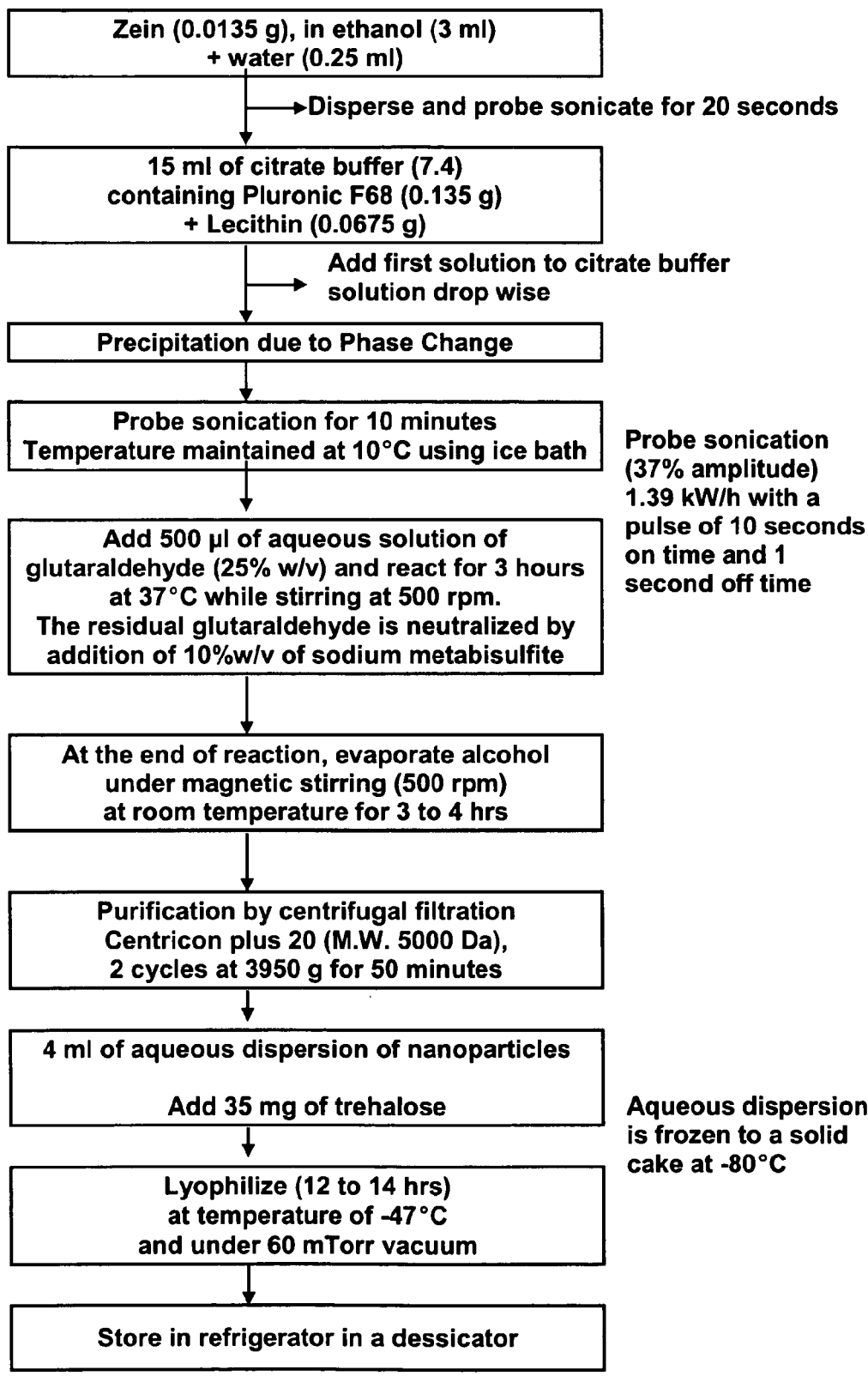
FIG. 17 illustrates by means of a flow chart a method of the present invention for preparing cross-linked blank zein nanoparticles.

In a further aspect of the present invention, the enzymatic stability of the nanoparticles produced by the disclosed methods of the invention can be further enhanced by cross-linking. FIG. 17 illustrates the general method for preparation of cross-linked blank zein nanoparticles using glutaraldehyde as the cross-linking agent. A specific example of such preparation is as follows:

Example VIII

Blank zein nanoparticles were prepared using the disclosed nanoprecipitation method. A cross linking agent was added following probe sonication of the second aqueous phase. Nanoparticles were further incubated for 24 hours. At the end of incubation time, the nanoparticles were purified using centrifugal filtration and were then lyophilized.

White zein in the amount of 0.0135 g was dissolved in a mixture of 3 ml of ethanol and 0.25 ml of water. The first phase solution was then added drop-wise into 15 ml of citrate buffer having a pH 7.4 and containing a combination of 0.45% w/v lecithin and Pluronic® F68 (0.9% w/v) under constant application of ultrasonic energy at 1.39 kW/h and 37% amplitude for 10 minutes with a pulse on-time of 10 seconds and off-time of 1 second. During the sonication process, the solution was kept in an ice bath to maintain the temperature at about 10° C. To the solution was added 0.5 ml of glutaraldehyde of 25% w/v and the solution was incubated for 3 to 24 hrs at 37° C. while stirring at 300 to 500 rpm. The residual glutaraldehyde was neutralized with 10% w/v metabisulfite. Subsequently, the dispersion was placed on a magnetic stirrer at 300 to 500 rpm and at room temperature until the ethanol was completely evaporated. After complete evaporation of the alcohol, the nanoparticles were purified to remove the residual material. Purification was accomplished by repeated washing with pH 7.4 citrate buffer and ultracentrifugation, using centrifugal filter of MWt cut off of 5000 Da, at 3950 g for 50 minutes. To the aqueous suspension of nanoparticles was added 35 mg of trehalose and the solution was kept at −80° C. to form a solid cake. The material was then lyophilized at −47° C. and 60 mTorr vacuum for 12 to 14 hrs.

Notably, for other cross-linking agents such as EDC/NHS and genipin, when used in the method of FIG. 13, the reaction time can vary from 24 to 72 hours. The surface amino groups in zein are involved in cross-linking. Trinitro benzene sulfonic acid (TNBS) was used to estimate the free amino groups in zein before and after cross-linking. A standard curve was generated with increasing concentration of non-cross linked and cross-linked zein versus absorbance at 440 nm wavelength. Cross linking efficiency was calculated using the formula, % of Cross linking efficiency=$[a-b/a]\times 100$, where a=slope of non-cross lined zein versus absorbance, and b=slope of cross-linked zein versus absorbance. The concentration range of zein used for constructing the standard curve is 0.357 mg/ml to 12 mg/ml, and correlation coefficient is 0.9994.

Figure 18:
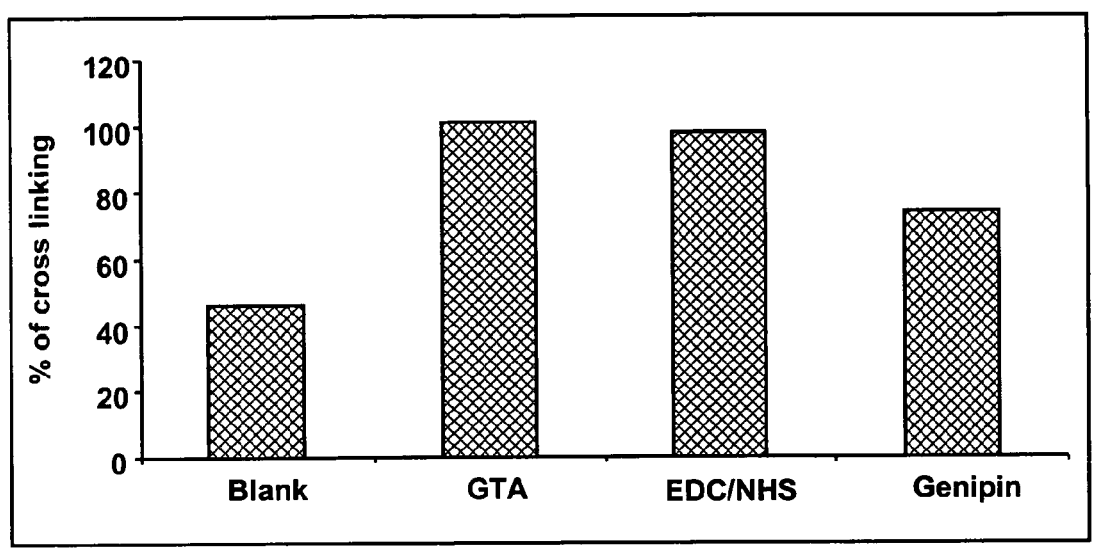
FIG. 18 is a graph demonstrating the extent of cross-linking of zein nanoparticles as a function of cross-linking agent for 24 hrs. The extent of cross-linking was determined using a TNBS assay. The cross-linking agents used were GTA-Glutaraldehyde (500 µl of a stock solution of 25% w/v), EDC: 1-Ethyl-3-[3-dimethylaminopropyl]carbodiimide (0.6% w/v), and NHS: N-hydroxyl succinimide (0.6% w/v). The concentration of genipin used was 0.05% w/v. "Blank" represents zein nanoparticles without any cross-linking agent. Data is a mean of two experiments.
Figure 19:
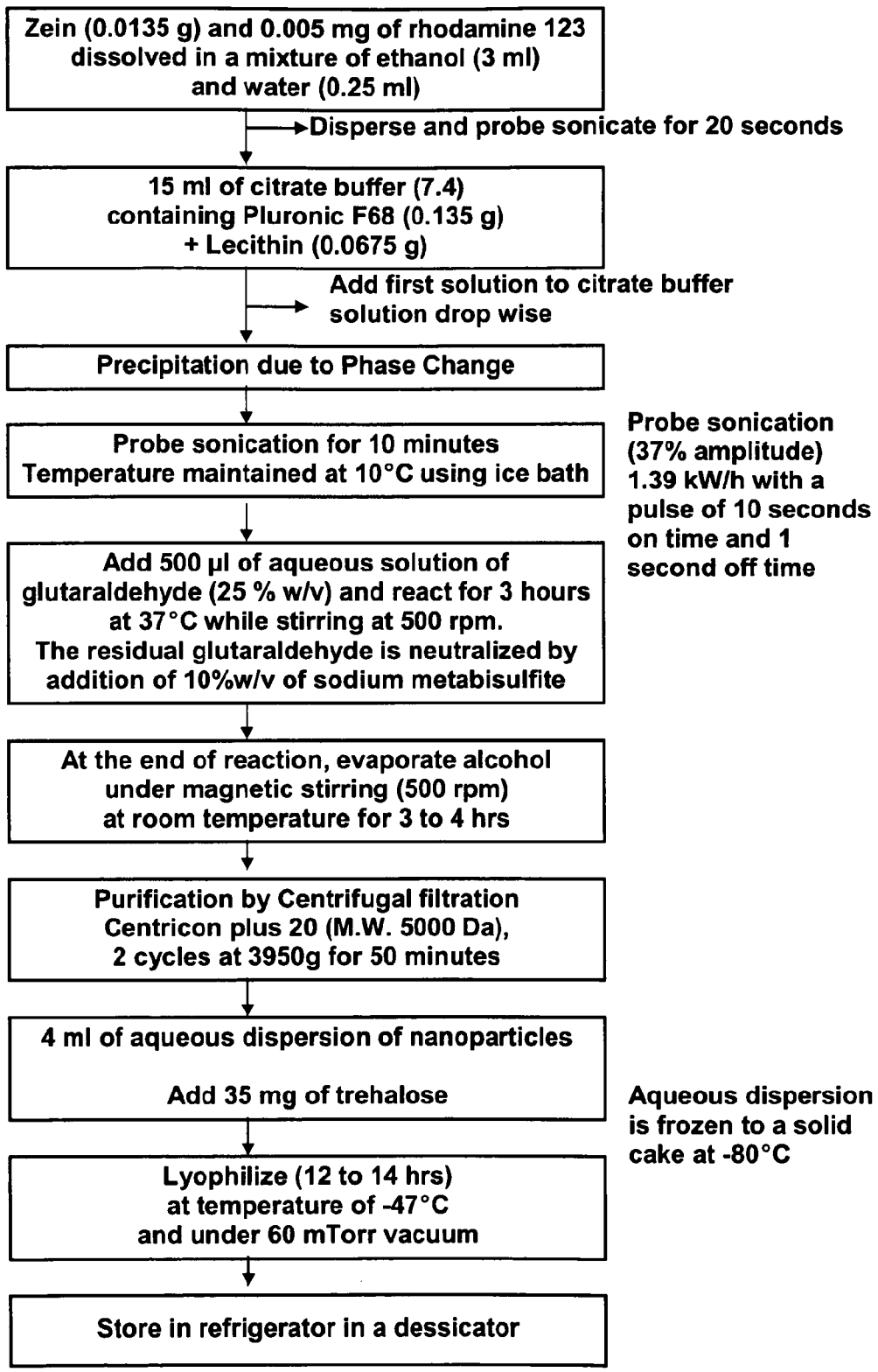
FIG. 19 illustrates by means of a flow chart a method of the present invention for preparing rhodamine-123-loaded cross-linked zein nanoparticles.

The extent of cross-linking in zein nanoparticles using different cross-linking agents is shown in FIG. 18. The cross-linking efficiency varied from approximately 70% to approximately 100%. The extent of cross-linking can be varied by changing the reaction time to range from approximately 3 hours to 3 days depending on the cross-linking agent. The cross-linking agent shown here are only examples and the methods of the invention are not limited to the use of just the disclosed cross-linking agents. Other cross-linking agents can be used such as polycarboxylic acids (citric acid or 1,2,3,4-butanetetracarboxylic acid).

Additionally, although the method is illustrated with respect to preparing blank zein nanoparticles, cross-linking may be provided in the formation of nanoparticles containing specific molecules. A specific example of preparing rhodamine, a water soluble dye, in a nanoparticle is as follows:

Example IX

White zein in an amount of 0.0135 g was dissolved in a mixture of 3 ml of ethanol and 0.25 ml of water (0.25 ml). To the first aqueous solution was added 0.005 g of rhodamine-123. The resulting solution was added drop-wise into 15 ml of citrate buffer having a pH 7.4 and containing a combination of 0.0675 g of lecithin and (0.135 g) of Pluronic® F68 under constant application of ultrasonic energy at 1.39 kW/h and 37% amplitude for 10 minutes with a pulse on-time of 10 seconds and off-time of 1 second. During the sonication process, the solution was kept in an ice bath to maintain the temperature at about 10° C. Then 0.5 ml of glutaraldehyde of 25% w/v was added and incubated for 3 hrs at 37° C. while stirring at 300 to 500 rpm.

The residual cross-linking agent was neutralized with 10% w/v sodium metabisulfite. Subsequently, the dispersion was placed on a magnetic stirrer at 300 to 500 rpm at room temperature until the ethanol was completely evaporated. After complete evaporation of the alcohol, the nanoparticles were purified ultracentrifugation. Purification was accomplished by repeated washing with pH 7.4 citrate buffer and ultracentrifugation using centrifugal filter of MWt cut off of 5000 Da, at 3950 g for 50 minutes. To the aqueous suspension (pH 7.4 citrate buffer) of rhodamine-loaded nanoparticles was added 35 mg of trehalose and the solution was kept at −80° C. to form a solid cake, which was then lyophilized at −47° C. and 60 mTorr vacuum for 12 to 14 hrs).

The particle size, polydispersity index and zeta potential of non-cross linked and cross-linked (using glutaraldehyde as cross-linking agent) rhodamine particles are shown in Table 6.

TABLE 6

| Model compound | Particle Size (nm) | Polydispersity index | Zeta potential (mV) |
|---|---|---|---|
| Rhodamine | 352 ± 20 | 0.72 ± 0.20 | −14 ± 7 |
| Rhodamine (cross linked particles) | 130 ± 35 | 0.72 ± 0.32 | −12 ± 2 |

Each value is a mean of three experiments (±SD).

Figure 20:
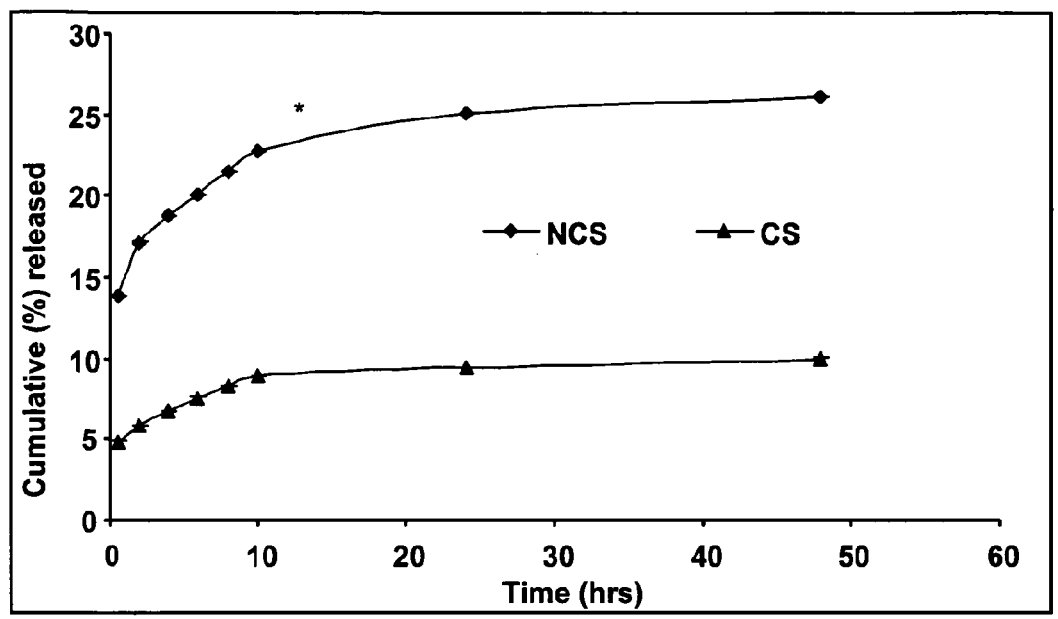
FIG. 20 illustrates the in vitro release profile of rhodamine-123 from zein nanoparticles in phosphate buffered saline (0.1 M) pH 7.4. Results represent mean±SEM (n=4). NCS=non-cross linked particles; CS=cross linked particles. The drug release from cross-linked nanoparticles was significantly (p>0.05) lower than the non cross-linked nanoparticles. Rhodamine-loaded zein nanoparticles (20 mg) prepared by the method of the present invention were placed in a dialysis membrane (Spectrapor™, M.wt. 10,000 Da) and incubated in 5 ml of phosphate buffered saline (pH 7.4). The solution was maintained at 37° C. in a horizontal shaker water bath at 100 rpm. An aliquot (1 ml) of the dialysate was removed at different time points over 48 hours and replaced with fresh media to maintain the sink conditions. Dialysate was analyzed for rhodamine release from the zein nanoparticles using spectrofluorimetry ($\lambda_{ex}$=485 nm; $\lambda_{em}$=530 nm).
Figure 21:
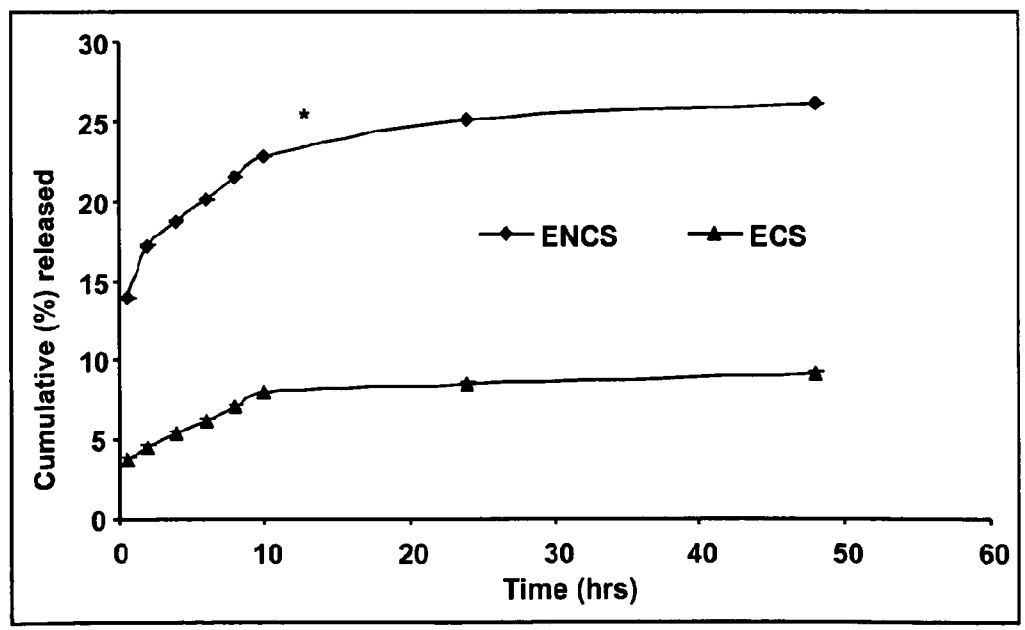
FIG. 21 illustrates the in vitro release profile of rhodamine-123 from zein nanoparticles in the presence of trypsin at pH 7.4. Results represent mean±SEM (n=4). ENCS=non-cross linked particles; ECS=cross linked particles. The drug release from cross-linked nanoparticles was significantly (p>0.05) lower than the non cross-linked nanoparticles. Rhodamine-123-loaded zein nanoparticles (20 mg) prepared by the method of the present invention were placed in a dialysis membrane (Spectrapor™, M.wt. 10,000 Da) and incubated in 5 ml of phosphate buffered saline (0.1M, pH 7.4) containing 205 µg/ml of trypsin. The solution was maintained at 37° C. in a horizontal shaker water bath at 100 rpm. An aliquot (1 ml) of the dialysate was removed at different time points over 48 hours and replaced with fresh media to maintain the sink conditions. Dialysate was analyzed for rhodamin-123 released from the zein nanoparticles using spectrofluorimetry ($\lambda_{ex}$=485 nm; $\lambda_{em}$=530 nm).

The in-vitro drug release at pH 7.4 is slower when the zein nanoparticles were cross-linked (FIG. 20) and similarly the enzymatic release was also slower (FIG. 21). The cross-linking of the free amino groups on the surface of zein nanoparticles reduced the particle size, and also reduced the access of solvent and slowed the enzymatic degradation of the nanoparticles. The cross-linking also significantly reduced the burst release. Thus cross-linking can further stabilize the nanoparticles and sustain the drug release.

The therapeutic activity and efficacy of the nanoparticles produced by the method of the invention, can be further enhanced by attaching polyethylene glycol (PEG) to the nanoparticles. Among the added benefits of PEGylation is an increase in the circulation half-life of the nanoparticles. An additional advantage of PEG is that it can serve as a spacer to link the targeting ligands, drugs, and imaging agents to zein nanoparticles, if direct conjugation is not feasible.

Figure 22:
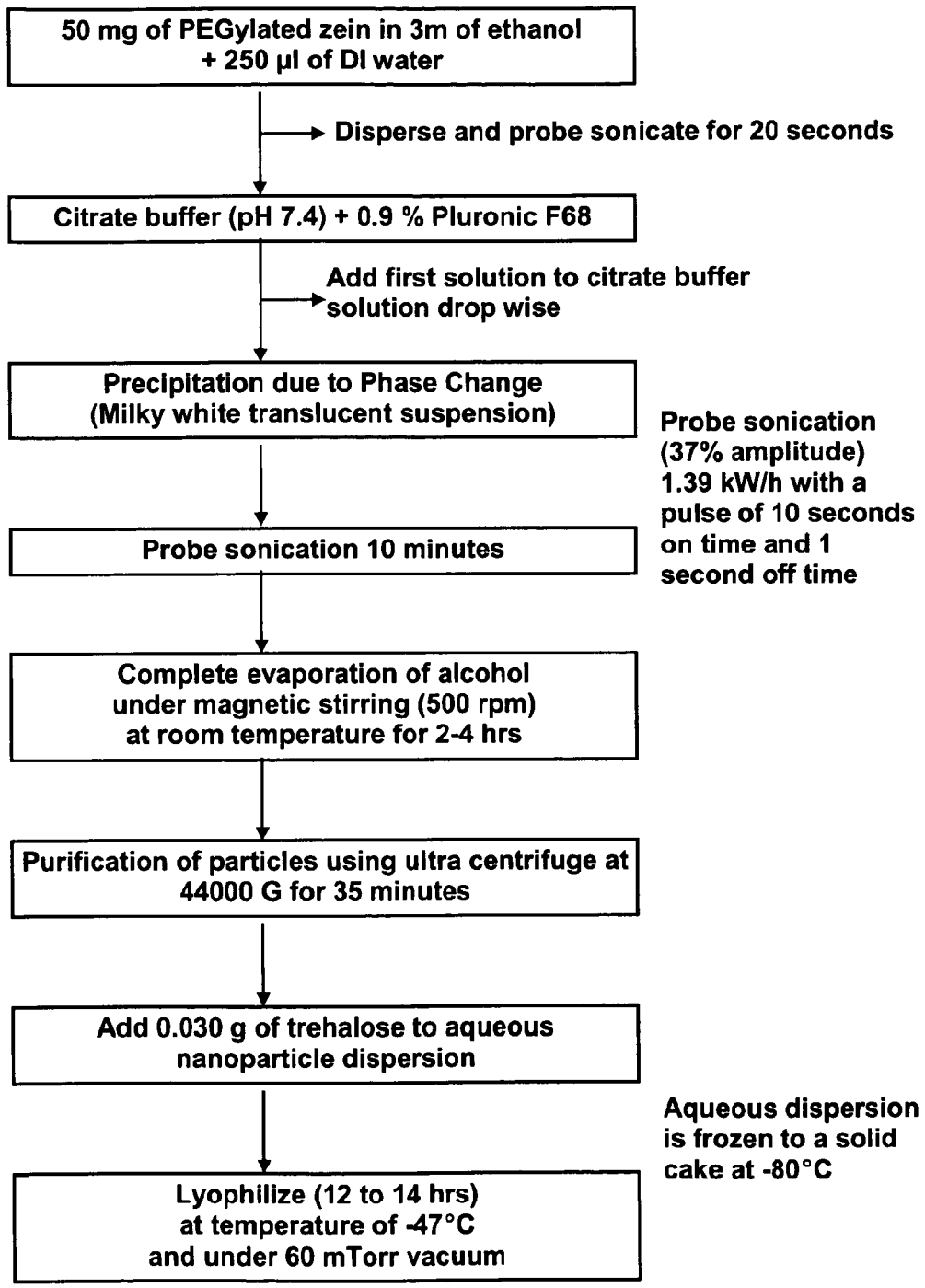
FIG. 22 illustrates in a flow chart the general method for preparation of blank PEGylated zein nanoparticles.

FIG. 22 illustrates a method of preparing PEGylated zein nanoparticles in accordance with another aspect of the method of the invention. An advantage of PEGylated zein for making nanoparticles is that it can be made using only a surfactant, such as Pluronic® F68, as opposed to the use of a combination of a surfactant and phospholipids for non-PE-Gylated zein. A specific method of forming PEGylated zein nanoparticles is as follows:

Example X

PEGylated zein was produced by adding 0.1 g of methoxy PEG-succinimidyl succinate (Mwt 5000 Da) to 0.1 g of white zein in 5 ml of 90% ethanol. The mixture was incubated for a period of between three hours and 24 hours at 37° C. The solution was then dialyzed (Mwt cut off 10,000 Da) against water in a magnetic stirrer (magnetic stir bar stirred at 100 rpm) at room temperature for 24 hours to remove any residual materials. The resulting product was then frozen to −80° C. followed by freeze drying at −47° C. at 60 mTorr vacuum for 12 to 14 hours. The efficiency of PEGylation observed over various incubation times is shown in Table 7, below, where the efficiency percentages were determined using a TNBS assay procedure as described earlier. Other molecular weight PEGs, such as from 500 to 5000 Da, can be used. Similarly PEG derivatives such as methoxy PEG-N-hydroxyl succinate ester or other derivatives can be used.

TABLE 7

| Incubation time (hrs) | Zein:mPEG ester ratio | PEGylation Efficiency (%) |
| --- | --- | --- |
| 24 | 1:1 | 65 |
| 24 | 1:2 | 93 |
| 3 | 1:1 | 52 |

Figure 23:
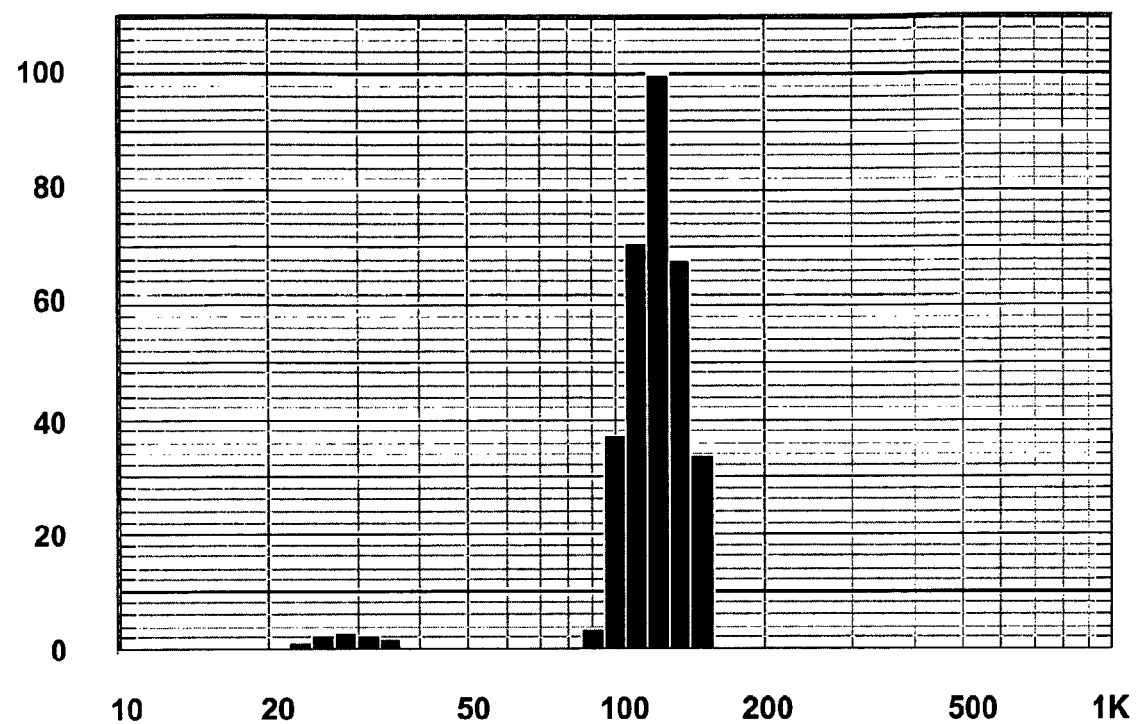
FIG. 23 is a graph illustrating an intensity of weighted size distribution of PEGylated nanoparticles. The particle size of PEGylated zein nanoparticles was 131±1 nm, with a Polydispersity Index (PDI) of 0.282±0.01. The data also shows that the surface modification of zein nanoparticles with PEG does not increase the particle size and that the nanoparticles are in the desired size range for drug delivery applications.

Fifty milligrams of PEGylated white zein were dissolved in a mixture of 3 ml ethanol and 0.25 ml deionized water. The PEGylated zein solution containing was then added dropwise into 15 ml of citrate buffer having a pH 7.4 and containing Pluronic® F68 (0.9% w/v) under constant application of ultrasonic energy at 1.39 kW/h and 37% amplitude for 10 minutes with a pulse on-time of 10 seconds and off-time of 1 second. During the sonication process the solution was maintained in an ice bath to maintain the temperature at about 10° C. Subsequently, the zein suspension was placed on a magnetic stirrer at 300 to 500 rpm at room temperature until the ethanol was completely evaporated. When evaporation was complete, the nanoparticles were purified. Purification was accomplished by repeated washing with pH 7.4 citrate buffer and ultracentrifugation using centrifugal filter of MWt cut off of 10000 Da, at 44,000 g for 35 minutes. To the aqueous suspension (pH 7.4 citrate buffer) of zein nanoparticles was added 30 g of 2% w/v trehalose and the solution was kept at −80° C. to form to solid cake, which was then lyophilized at −47° C. and 60 mTorr vacuum for 12 to 14 hrs. The PEGylation process disclosed above may be carried out using high pressure homogenization as disclosed in Example II, above. The size distribution of the PEGylated nanoparticles is shown in FIG. 23.

Because zein is a protein, a further advantage of using zein in formation of nanoparticles is realized in that zein has a large number of surface functional groups which can be used to attach targeting ligands, imaging agents, drugs and other polymers for drug targeting to specific tissues and other biomedical applications.

Zein nanoparticles formed using the disclosed method may have other uses, particularly outside of the body. For example, drug-loaded zein nanoparticles can be used as a coating material for cardiovascular and other biomedical devices. Although described herein with respect to drug delivery, nanoparticles produced by the disclosed method may be used to encapsulate and sustain the release of molecules of interest to the food, dairy and cosmetic industries as well. In addition to human drugs, veterinary drugs may also be encapsulated in nanoparticles using the disclosed methods. Zein nanoparticles may be used to protect molecules from adverse environmental agents such as moisture, oxidation, light etc. This utilization may include molecules of interest to the pharmaceutical, food, dairy and cosmetic industries.

Zein can be combined with other natural and synthetic polymers to design novel nanoparticles with unique properties for various applications in the biomedical, pharmaceutical, food, dairy and cosmetic industry. For example, by attaching a pH-sensitive polymer or linker to zein, the zein nanoparticles can be made to release the drug in response to a pH stimulus.

All references, including publications, patents, and patent applications, cited herein are hereby incorporated by reference to the same extent as if each reference were individually and specifically indicated to be incorporated by reference and were set forth in its entirety herein, including:

1. H. Bernstein, E. Morrel, E. Mathowitz, K. Shwaller, T. R. Beck. Protein microspheres and methods of using them. U.S. Pat. No. 5,679,377 issued Oct. 21, 1997.
2. X. Liu, Q. Sun, H. Wang, L. Zhang, J. Y. Wang. Microspheres of corn protein, zein, for an ivermectin drug delivery system. Biomaterials 26 (2005) 109-115.
3. P. H. López, S. Murdan. Zein microspheres as drug/antigen carriers: A study of their degradation and erosion, in the presence and absence of enzymes. J. Microencapsulation 23 (2006) 303-314.
4. Q. Zhong, M. Jin, D. Xiao, H. Tian, W. Zhang. Application of supercritical anti-solvent techniques for syntheses of delivery systems of bioactive food components. Food. Biophysics 3 (2008) 186-190.
5. N. Parris, P. H. Cooke, K. B Hicks. Encapsulation of Essential Oils in Zein Nanospherical Particles. J. Agric. Food. Chemistry 53 (2005) 4788-4792.
6. L. E. Stark, A. T. Gross. Hydrophobic protein microparticles. U.S. Pat. No. 5,330,778 issued Jul. 19, 1994.
7. S. Rudt, R. H. Müller. In vitro phagocytosis assay of nano- and microparticles by chemiluminescence. II. Effect of surface modification by coating of particles with poloxamer on the phagocytic uptake. J. Control. Release. 25 (1993) 51-59.
8. P. H. Lopez, S. Murdan. An investigation into the immunogenicity and adjuvanticity of zein microspheres used as vaccine carriers. J. Pharm. Pharmacol. 58 (2006) 769-774.
9. R. B. Cook, F. M. Mallee, M. L. Shulman. Purification of zein from corn gluten meal. U.S. Pat. No. 5,245,673 issued Oct. 19, 1993.
10. E. Y. Shalaev, T. D. Johnson-Elton, L. Chang, M. J. Pikal. Thermophysical Properties of Pharmaceutically Compatible Buffers at Sub-Zero Temperatures: Implications for Freeze-Drying. Pharm. Res. 19 (2002) 195-201.
11. N. Reddy, Y. Li, Y. Yang. Alkali-catalyzed low temperature wet crosslinking of plant proteins using carboxylic acids. Biotechnol. Prog. 25 (2009) 139-146.
12. Wheat gluten, corn gluten and zein film: affirmation of GRAS status. Fed. Register 50 (1985) 8997-8999.

What is claimed is:

1. A therapeutically-active, non-immunogenic nanoparticle formed by a method comprising:
   providing a prolamine;
   dissolving said prolamine with a hydroalcoholic solvent to provide a first aqueous phase solution and adding to said prolamine in the formation of the first phase solution a molecule that is selected for nanoparticle encapsulation;
   adding a buffering agent to the first aqueous phase solution in the presence of a surfactant and a phospholipid to produce a second aqueous phase solution having a pH of between approximately pH 6.8 and approximately pH 7.4;
   processing said second aqueous phase solution to effect a reduction in diameter size of particles within the solution;
   evaporating any residual solvent to produce nanoparticles having a diameter size of less than about 400 nm;
   and isolating said nanoparticles;
   wherein the nanoparticle consists essentially of a prolamine, a phospholipid, a surfactant, and a therapeutic or diagnostic agent.

2. A therapeutic composition comprising a non-immunogenic nanoparticle formed by the encapsulation of a therapeutic molecule in a prolamine, said nanoparticle having a size diameter of less than about 400 nm, wherein the nanoparticle consists essentially of a prolamine, a phospholipid, a surfactant, and said therapeutic molecule, and wherein said nanoparticle does not aggregate after lyophilization.

3. The therapeutic composition according to claim 2 wherein said diameter size of said nanoparticle is between about 100 nm and about 300 nm, wherein the therapeutic molecule is selected from the group consisting of a small molecular drug, nucleic acids, protein, vaccine, antibody, and an anticancer agent, and wherein the prolamine is zein.

4. A kit for producing non-immunogenic nanoparticles, comprising:
   a selected amount of a prolamine;
   a hydroalcoholic solvent for dissolving said prolamine;
   at least one buffering agent;
   at least one selected phospholipid;
   optionally, a therapeutic agent, diagnostic agent, or probe; and
   a selected surfactant.

5. The kit according to claim 4, wherein resulting nanoparticles consist essentially of zein, a phospholipid, a surfactant, and optionally a therapeutic agent, diagnostic agent, or probe, and wherein said resulting nanoparticles do not aggregate after lyophilization.

* * * * *